United States Patent
Lee et al.

(10) Patent No.: US 7,070,682 B2
(45) Date of Patent: Jul. 4, 2006

(54) MICROFLUIDIC APPARATUS FOR PERFORMING GEL PROTEIN EXTRACTIONS AND METHODS FOR USING THE APPARATUS

(76) Inventors: Cheng Lee, 3823 Grosvenor Dr., Ellicott City, MD (US) 21042; Don DeVoe, 5619 Sonoma Rd., Bethesda, MD (US) 20817

( * ) Notice: Subject to any disclaimer, the term of this patent is extended or adjusted under 35 U.S.C. 154(b) by 758 days.

(21) Appl. No.: 10/047,759

(22) Filed: Jan. 15, 2002

(65) Prior Publication Data

US 2002/0121444 A1 Sep. 5, 2002

Related U.S. Application Data

(60) Provisional application No. 60/261,215, filed on Jan. 16, 2001, and provisional application No. 60/287,754, filed on May 1, 2001.

(51) Int. Cl.
  *G01N 27/447* (2006.01)
  *G01N 27/453* (2006.01)

(52) U.S. Cl. ................. 204/462; 204/613
(58) Field of Classification Search ......... 204/462, 204/450, 456, 466, 600, 606, 613, 616, 615, 204/465
See application file for complete search history.

(56) References Cited

U.S. PATENT DOCUMENTS

| | | | |
|---|---|---|---|
| 4,576,702 A | 3/1986 | Peck et al. | 204/299 |
| 5,066,377 A | 11/1991 | Rosenbaum et al. | 204/182.8 |
| 5,102,518 A | 4/1992 | Doering et al. | 204/180.1 |
| 5,217,591 A | 6/1993 | Gombocz et al. | 204/299 |
| 5,245,185 A | 9/1993 | Busch et al. | 250/288 |
| 5,275,710 A | 1/1994 | Gombocz et al. | 204/299 |
| 5,505,831 A | 4/1996 | Liao et al. | 204/451 |
| 5,541,420 A | 7/1996 | Kambara | 204/602 |
| 5,587,062 A | 12/1996 | Togawa et al. | 204/613 |
| 5,599,432 A | 2/1997 | Manz et al. | 204/451 |
| 5,635,045 A | 6/1997 | Alam | 204/462 |
| 5,795,720 A | 8/1998 | Henco et al. | 435/6 |
| 5,916,428 A | 6/1999 | Kane et al. | 204/601 |
| 5,957,579 A | 9/1999 | Kopf-Sill et al. | 366/340 |
| 6,013,165 A | 1/2000 | Wiktorowicz et al. | 204/456 |
| 6,068,752 A | 5/2000 | Dubrow et al. | 204/604 |
| 6,274,089 B1 | 8/2001 | Chow et al. | 422/101 |
| 6,406,604 B1 | 6/2002 | Guzman | 204/601 |
| 6,540,896 B1 | 4/2003 | Manz et al. | 204/451 |
| 6,592,735 B1 | 7/2003 | Meier et al. | 204/621 |

FOREIGN PATENT DOCUMENTS

| | | |
|---|---|---|
| WO | WO 94/28406 | 12/1994 |
| WO | WO 98/00231 | 1/1998 |
| WO | WO 00/57170 | 9/2000 |

OTHER PUBLICATIONS

CAPLUS abstract for Domingo (ES 2078878 A1).
CAPLUS abstract for Grushka et al. ("Effect of Temperature Gradients on the Efficiency of Capillary Zone Electrophoresis Separations", *Analytical Chemistry*, (1989), 61(3); 241–6).
CAPLUS abstract for Guttman et al.("Effect of Temperature on the Seperation of DNA Restriction Fragments in Capillary Gel Electrophoresis", *Journal of Chromatography*, (1991), 559(1–2); 285–94).

(Continued)

*Primary Examiner*—Alex Noguerola
(74) *Attorney, Agent, or Firm*—Pillsbury Winthrop LLP

(57) ABSTRACT

The invention relates to an apparatus for performing gel protein extractions and methods of using the apparatus.

75 Claims, 10 Drawing Sheets

Schematic of component-level platform for rapid and sensitive identification of proteins resolved on polyacrylamide gels.

OTHER PUBLICATIONS

CAPLUS abstract for Zhang et al. ("The Effect of Column Temperature on the Migration Teimes of Peptides in Free-Solution Capillary Electrophoresis", *Journal of Liqiud Chromatogrphy*, (1993), 16(17): 3689–97.

Gao et al., "High—Throughput Detection of Unknown Mutations by Using Multiplexed Capillary Electrophoresis with Poly(vinylpyrrolidone) Solutions",*Analytical Chemical*, vol. 72, No. 11, Jun. 1, 2000, pp. 2499–2506.

Gottschlich et al., "Two–dimensional Electrochromatography/Capillary Electrophoresis on a Microchip", *Analytical Chemistry*, vol. 73, No. 11, Jun. 1, 2001, pp. 2669–2674.

Rocklin et al., "A Microfabricated Fluidic Device for Performing Two–Dimensional Liquid–Phase Separations", *Analytical Chemistry*, vol. 72, No. 21, Nov. 1, 2000, pp. 5244–5249.

Becker et al., "Planar Quartz Chips with Submicron Channels for Two–Dimensional Capillary Electrophoresis Applications", *J. Micromech. Microeng.*, vol. 8, 1998, pp. 24–28.

Liu et al., "Two–Dimensional Separations: Capillary Electrophoresis Coupled to Channel Gel Electrophoresis", *Analytical Chemistry*, vol. 68, No. 22, Nov. 15, 1996 pp. 3928–3933.

Hillenkamp et al., "Matrix–Assisted Laser Desorption/Ionization Mass Spectrometry of Biopolymers", *Analytical Chemistry*, vol. 63, No. 24, Dec. 15, 1991, pp. 1193A–1202A.

Fenselau, "MALDI–MS and Strategies for Protein Analysis", *Analytical Chemistry News& Features*, vol. 69, Nov. 1, 1997, pp. 661A–665A.

Kebarle et al., "From Ions in Solution to Ions in the Gas Phase—The Mechanism of Electrospray Mass Spectrometry", *Analytical Chemistry*, vol. 65, No. 22, Nov. 15, 1993, pp. 972A–986A.

Yates, III, "Special Feature: Tutorial: Mass Spectrometry and the Age of the Proteome", *Journal of Mass Spectrometry*, vol. 33, 1998, pp. 1–19.

Klose et al., "Two–Dimensional Electrophoresis of Proteins: An Updated Protocol and Implications for a Functional Analysis of the Genome",*Electrophoresis*, vol. 16, 1995, pp. 1034–1059.

Jungblut et al., "Resolution Power of Two–Dimensional Electrophoresis and Identification of Proteins from Gels", *Electrophoresis*, vol. 17, 1996, pp. 839–847.

Rabilloud, "Detecting Proteins Separated by 2–D Gel Electrophoresis",*Analytical Chemistry*, vol. 72, Jan. 1, 2000, pp. 48A–55A.

Shevchenko et al., "Mass Spectrometric Sequencing of Proteins from Silver–Stained Polyacrylamide Gels", *Analytical Chemistry*, vol. 68, No. 5, Mar. 1, 1996, pp. 850–858.

Shevchenko et al., "Linking Genome and Proteome by Mass Spectrometry: Large–Scale Identification of Yeast Proteins from Two Dimensional Gels", *Proc. Natl. Acad. Sci. USA*, vol. 93, Dec. 1996, pp. 14440–14445.

Gygi et al., "Evaluation of Two–Dimensional Gel Electrophoresis–Based Proteome Analysis Technology", *Proc. Natl. Acad. Sci. USA*, vol. 97, No. 17, Aug. 15, 2000, pp. 9390–9395.

Smith, "Probing Proteomes—Seeing the Whole Picture?", *Nature Biotechnology*, vol. 18, Oct. 2000, pp. 1041–1042.

Burgi et al., "Optimization in Sample Stacking for High–Performance Capillary Electrophoresis", *Analytical Chemistry*, vol. 63, No. 18, Sep. 15, 1991, pp. 2042–2047.

Chien et al., "On–Column Sample Concentration Using Field Amplification in CZE", *Analytical Chemistry*, vol. 64, No. 8, Apr. 15, 1992, pp. 489A–496A.

Chien et al., "Sample Stacking of an Extremely Large Injection Volume in High–Performance Capillary Electrophoresis", *Analytical Chemistry*, vol. 64, No. 9, May 1, 1992, pp. 1046–1050.

Burgi et al., "On–Line Sample Preconcentration for Capillary Electrophoresis", in *Handbook of Capillary Electrophoresis*, Edited by James P. Landers, CRC Press, 1997, pp. 479–493.

Ramsey et al., "Generating Electrospray from Microchip Devices Using Eletroosmotic Pumping", *Analytical Chemistry*, vol. 69, No. 6, Mar. 15, 1997, pp. 1174–1178.

Oleschuk et al., "Analytical Microdevices for Mass Spectrometry", *Trends in Analytical Chemistry*, vol. 19, No. 6, 2000, pp. 379–388.

Gatlin et al., "Protein Identification at the Low Femtomole Level from Silver–Stained Gels Using a New Fritless Electrospray Interface for Liquid Chromatography—Microspray and Nanospray Mass Spectrometry", *Analytical Biochemistry*, vol. 263, 1998, Article No. AB982809, pp. 93–101.

Scheler et al., "Peptide Mass Fingerprint Sequence Coverage from Differently Stained Proteins on Two–Dimensional Electrophoresis Patterns by Matrix Assisted Laser Desorption/Ionization–Mass Spectrometry (MALDI–MS)", *Electrophoresis*, vol. 19, 1998, pp. 918–927.

Ramsamooj et al., "Differential Expression of Proteins in Radioresistant and Radiosensitive Human Squamous Carcinoma Cells," *Journal of the National Cancer Institute*, vol. 84, No. 8, Apr. 15, 1992, pp. 622–628.

Wilkins et al., "Proteome Research: New Frontiers in Functional Genomics", Published by Springer, Berlin, 1997, pp. 187–219.

Ostergaard et al., "Psoriasin (S100A7): A Putative Urinary Marker for the Follow–Up of Patients with Bladder Squamous Cell Carcinomas", *Electrophoresis*, vol. 20, 1999, 349–354.

Page et al., "Proteomic Definition of Normal Human Luminal and Myoepithelial Breast Cells Purified from Reduction Mammoplasties", *Proc. Natl. Acad. Sci. USA*, vol. 96, No. 22, Oct. 26, 1999, pp. 12589–12594.

Wilm et al., "Femtomole Sequencing of Proteins from Polycrylamide Gels by Nano–Electrospray Mass Spectrometry", *Nature*, vol. 379, Feb. 1, 1996, pp. 466–469.

Lottspeich, "Proteome Analysis: A Pathway to the Functional Analysis of Proteins", *Angew. Chem. Int. Ed.*, vol. 38, 1999, pp. 2476–2492.

Pandey et al., "Proteomics to Study Genes and Genomes", *Nature*, vol. 405, Jun. 15, 2000, pp. 837–846.

Binz et al., "A Molecular Scanner to Automate Proteomic Research and to Display Proteome Images", *Analytical Chemistry*, vol. 71, No. 21, Nov. 1, 1999, pp. 4981–4988.

Bienvenut et al., "Toward a Clinical Molecular Scanner for Proteome Research: Parallel Protein Chemical Processing Before and During Western Blot", *Analytical Chemistry*, vol. 71, No. 21, Nov. 1, 1999, pp. 4800–4807.

Hjerten et al., "Adaptation of the Equipment for High–Performance Electrophoresis to Isoelectric Focusing", *Journal of Chromatography*, vol. 346, 1985, pp. 265–270.

Hjerten et al., "Carrier–Free Zone Electrophoresis, Displacement Electrophoresis, and Isoelectric Focusing in a High–Performance Electrophoresis Apparatus", *Journal of Chromatography*, vol. 403, 1987, pp. 47–61.

Kilar et al., "Fast and High Resolution Analysis of Human Serum Transferrin by High Performance Isoelectric Focusing in Capillaries", *Electrophoresis*, vol. 10, 1989, pp. 23–29.

Yefimov et al., "Transfer of SDS–Proteins from Gel Electrophoretic Zones into Mass Spectrometry, Using Electroelution of the Band into Buffer Without Sectioning of the Gel", *Journal of Biochemical and Biophysical Methods*, vol. 42, 2000, pp. 65–78.

Yefimov et al., "Recovery of Sodium Dodecyl Sulfate–Proteins from Gel Electrophoretic Bands in a Single Electroelution Step for Mass Spectrometry Analysis", *Analytical Biochemistry*, vol. 284, 2000, pp. 288–295.

Galvini et al., "Letter to the Editor", *Rapid Communications in Mass Spectrometry*, vol. 14, 2000, pp. 721–723.

Clarke et al., "One Stpe Microelectroelution Concentration Method for Efficient Coupling of Sodium Dodacylsulfate Gel Electrophoresis and Matrix–Assisted Laser Desorption Time–of–Flight Mass Spectrometry for Protein Analysis", *Journal of the American Society of Mass Spectrometry*, vol. 9, 1998, pp. 88–91.

Tomlinson et al., Improved On–Line Membrane Preconcentration—Capillary Electrophoresis (mPC–CE), *Journal of High Resolution Chromatography*, vol. 18, Jun. 1995, pp. 381–383.

Timperman et al., "Peptide Electroextraction for Direct Coupling of In–Gel Digests with Capillary LC—MS/MS for Protein Identification and Sequencing", *Analytical Chemistry*, vol. 72, No. 17, Sep. 1, 2000, pp. 4115–4121.

Guttman et al., "Rapid Analysis of Covalently and Non–Convalently Fluorophore–Labeled Proteins Using Ultra–Thin–Layer Sodium Dodecylsulfate Gel Electrophoresis", *Journal of Chromatography A*, vol. 894, 2000, pp. 329–335.

Csapo et al., "Automated Ultra–Thin–Layer SDS Gel Electrophoresis of Proteins Using Noncovalent Fluorescent Labeling", *Analytical Chemistry*, vol. 72, No. 11, Jun. 1, 2000, pp. 2519–2525.

Shoji et al., "Electrophoretic Recovery of Proteins from Polyacrylamide Gel", *Journal of Chromatography A*, vol. 698, 1995, pp. 145–162.

FIG. 1 Schematic of gel protein extraction apparatus

FIG. 2 Schematic of component-level platform for rapid and sensitive identification of proteins resolved on polyacrylamide gels.

Fig. 3 Electropherograms of (A) electrokinetically injected SDS-cytochrome C complex in CZE with a concentration of 0.5 mg/ml and (B) extracted SDS-cytochrome C complex from SDS-PAGE with a protein loading of 100 ng.

Fig. 4 (a) exploded view of a gPEP cartridge, and (b) assembled cartridge including laser-induced fluorescence detection system (drawings not to scale).

Dependence of peak heights of extracted proteins upon protein mass loadings.

Reaction temperature dependence of trypsin digestion in a PVDF membrane at a sample flow rate of 0.3 ml/min: (A) 40°C and (B) 50°C.

Protein concentration dependence of trypsin digestion in a PVDF membrane at room temperature and a sample flow rate of 0.3 ml/min: (A) 0.1 mg/ml and (B) 10 mg/ml.

The positive ESI mass spectrum of extracted and digested cytochrome C peptides.

MICROFLUIDIC APPARATUS FOR PERFORMING GEL PROTEIN EXTRACTIONS AND METHODS FOR USING THE APPARATUS

RELATED APPLICATIONS

This application claims priority from U.S. Ser. No. 60/261,215, filed Jan. 16, 2001, and U.S. Ser. No. 60/287,754, filed May 1, 2001, which are incorporated by reference in their entirety.

FIELD OF THE INVENTION

The invention relates to an apparatus for performing gel protein extractions and methods of using the apparatus.

BACKGROUND OF THE INVENTION

Complex biological processes, including development, differentiation, and signal transduction, involve the coordinated expression of multiple genes and proteins, as well as control of their function. The identification and quantification of multiple proteins that constitute and control a particular process is important for understanding the regulation of biological systems. Additionally, the ability to monitor the presence or absence of particular proteins, an increase or decrease in protein expression, a change in protein microheterogeneity, or a combination of these modifications may be used for early diagnosis of a wide spectrum of known diseases (1). Proteomics, the large-scale analysis of proteins, will therefore contribute greatly to our understanding of gene function in the post-genomics era.

There are several known methods for analyzing proteins in the developing field of proteomics. All of these, however, have certain disadvantages associated with them. One currently used tool for protein identification and sequencing is mass spectrometry (MS) employing matrix-assisted laser desorption/ionization (MALDI) (2,3) and electrospray ionization (ESI) (4,5). For the analysis of complex protein mixtures such as cell lysates, two-dimensional polyacrylamide gel electrophoresis (2-D PAGE) is still the method of choice for separating more than thousands of proteins (6,7,8) prior to MALDI-MS or ESI-MS. Prior to mass spectrometric analysis, individual protein spots are excised from the gel, washed, in-gel reduced, S-alkylated, and in-gel digested with an excess of trypsin. Repeated washing, drying, and swelling of gel pieces are needed between each step of chemical or enzymatic reaction. Peptides are then extracted using aqueous/organic mixtures at acidic or basic conditions and prepared for peptide mass mapping or sequencing using MALDI or ESI-MS (9,10). All of these procedures are time-consuming tasks prone to sample loss and analyte dilution.

Due to its ability to provide detailed views of thousands of proteins expressed by an organism or cell type. 2-D PAGE has been a primary tool for comparative studies of proteins, for example, between normal and cancerous cells (44,45,46,47). The two dimensions of a 2-D PAGE separation are isoelectric focusing in a pH gradient and SDS-PAGE. Each protein spot provides a rough measure of isoelectric point (pI) and molecular weight of the protein within 5–10%. Extremely high resolution of 2-D PAGE for protein separation is achieved by working under denaturing conditions. Attempts to perform native 2-D electrophoresis result in 2-D protein patterns with poor reproducibility, smears, and less distinct protein spots (7). In addition, the advantages of SDS-PAGE are that virtually all proteins are soluble in SDS and the range of relative molecular mass from 10,000 to 300,000 is readily covered. 2-D PAGE has assumed a major role in "proteomics".

However, 2-D PAGE is a relatively slow, labor intensive, and cumbersome technology. Presently, protein identification and the study of protein modifications generally involve the separate excision, proteolytic digestion, peptide extraction, and mass spectrometric analysis of each "spot" (5,9,10,11,48,49,50). Concomitant sensitivity limitations are introduced by the necessary sample handling. Other approaches include the use of thin gel for direct protein identification (51) and membrane electroblotting for protein transfer, followed by direct protein scanning or on-membrane proteolytic digestion and peptide detection using MALDI-MS (52,53,54,55). Moreover, 2-D PAGE results from different laboratories can be difficult to compare, and sensitivity is limited by the amount of a protein needed to visualize a spot, typically in the low-nanogram range for silver staining.

A recent study (11), has demonstrated a disadvantage of 2-D PAGE in that only the higher abundance proteins were identified by the 2-D PAGE-MS strategies. The results indicated that more than half of all yeast proteins with lower abundance were not amenable to be studied by current 2-D PAGE-MS approaches. This conclusion is consistent with the combined results of other yeast proteome 2-D PAGE-MS studies that have yielded a combined total of only ~500 identified proteins. Thus, important classes of regulatory proteins involved in signal transduction and gene expression, for example, and other lower abundant proteins remain unidentified by the current 2-D PAGE-MS methodologies.

One obvious approach to increase the detection capability of low abundant proteins is to raise the protein loading from 0.5 mg to 50 mg, clearly exceeding the capacity of 2-D PAGE (11). The extracted peptides from the spots on SDS-PAGE are fractionated and analyzed using various chromatography techniques and MS/MS. Another approach will be to separate the proteins into a number of fractions before 2-D PAGE in addition to the use of a series of narrow pH range gels (12). The disadvantage of these strategies, however, is that they all require much larger amounts of protein along with many additional 2-D PAGE and chromatography separations, and therefore may be impractical for studies of small cell populations or tissue samples.

Thus, significant research efforts have been reported in the literature toward providing better linkage between 2-D PAGE and mass spectrometric analysis. For example, Ekstrom et al. (56) have combined several silicon micromachined analytical tools, including the microchip immobilized enzyme reactor, the piezoelectric microdispenser, and the high-density nanovial target plates, into an integrated platform for performing rapid protein digestion and subsequent picoliter sample preparation in a high-density format for MALDI-MS. Harrison and coworkers (57) have reported the integration of immobilized trypsin beads within a glass chip for protein digestion followed by on-chip capillary electrophoresis separations and ES-IMS detection.

Togawa et al., (77), Gombocz et al., (78,79), Doering et al., (80), Peck et al., (81), Kambara et al., (83), and Yefimov et al., (84) all disclose apparatuses for extracting protein from a gel. However, none of these disclose methods of increasing the speed of transfer, or supply methods of concentrating the transferred proteins. Liao et al., (82) describe a method for concentrating proteins, but not methods relating to 2D gel electrophoresis.

Still, the limiting factor for linking 2-D PAGE with mass spectrometric analysis lies in the effective and rapid recovery of peptides, in particular those from low-abundance proteins, from in-gel digestion as well as the extraction and the transfer of gel proteins for sequential or parallel proteolytic digestion (9,58,59). There is a need in the art for a method of rapidly recovering low abundance peptides from 2-D gel electrophoresis. This invention satisfies that need by providing apparatus and methods for performing gel extractions.

SUMMARY OF THE INVENTION

The invention is directed to a microfluidic apparatus and methods for performing gel protein extractions using the apparatus. The invention involves rapid and efficient extraction of protein analytes directly from 2-D gels using their electrophoretic mobilities, or willingness of a molecule to migrate in accordance with its charge under the application of an electric field in a conductive solution based medium. It is possible to sequentially or simultaneously mobilize several proteins out of gel electrophoresis media and into an apparatus with fluidic channels filled with an electrolyte solution under the application of a high electric field. Once inside the fluidic channels, proteins can be transferred to a miniaturized membrane digestion reactor by pressure or electrokinetic means. The peptide fragments from each protein analyte can be further introduce into a mass spectrometer through fluidic components for protein identification and quantification.

In order to identify the minor proteins being expressed by the cells, the present invention involves no manual sample transfer or dilution steps. Additionally, concentration of extracted proteins in the fluidic channels can be achieved using electrokinetic stacking. The present apparatus in combination with mass spectrometry will allow automated, rapid, high resolution, and high throughput identification and quantification of proteins separated in a 2-D gel for proteomics analysis.

One embodiment of the invention is a microfluidic apparatus comprising a housing with a cover, the cover being capable of pressurization. The cover contains one or more holes, apertures, or ports, through which is disposed a sleeve, a single sleeve fitting within a single hole. Disposed through the cover through the sleeve is a fluidic channel. In some embodiments a single fluidic channel is disposed trough the cover and sleeve. In other embodiments a plurality of fluidic channels are disposed therethrough.

Inside the housing is placed a gel, containing one or more proteins to be extracted, and an electrolyte solution. The gel can be made of a variety of suitable materials, including polyacrylamide or agarose, and can be a variety of thicknesses, preferably between about 100 μm and about 1 mm thick. In another embodiment, the gel can be a gradient gel ranging from about 4% to about 20% polyacrylamide, and can be composed of Tris/Tricine SDS polyacrylamide.

In some embodiments, the gel could have been used for 1D or 2D gel electrophoresis. The electrolyte solution covering the gel and in the housing can be selected from a variety of materials, including buffers. In one embodiment, the electrolyte solution is Tris-HCL with a concentration up to 25 mM, at about pH 6.8.

The housing also contains a ground electrode. One end of one or many fluidic channels, containing electrolyte solution, are passed through the cover into the housing, and secured at the surface of the gel. The second end(s) of the fluidic channel(s) are located in a separate outlet reservoir of electrolyte solution. An outlet electrode is also located in this reservoir, which can be of any suitable materials, including platinum or gold. In some embodiments, the electrode is made of a thin film of metal that is placed into a glass or plastic substrate.

In some embodiments, a detector is placed adjacent to the fluidic channel near the outlet reservoir for monitoring extracted proteins. More preferably, the detector can be a UV absorbance detector or a fluorescence emission detector.

A high voltage power supply is electrically connected to the outlet electrode for applying an electric field across the length of the fluidic channel. This electric field can vary in strength, preferably between about 100 to about 1000 V/cm. As stated above, either a single or multiple fluidic channels may be used. If multiple channels are used, the channels can be connected to the high voltage power supply through an array of switches allowing different channels to be activated separately or simultaneously.

In another embodiment of the invention, the fluidic channels are capillaries, or more specifically, fused silica capillaries. The capillaries are also microscale in diameter. They have outer diameters ranging from about 100 to about 500 μm, and inner diameters that range from about 5 to about 100 μm. The channels can be of any length, preferably ranging between about 1 and 50 cm. The channels can be constructed of any suitable substrates, including a planar glass or planar plastic substrate. In some embodiments, the channels are coated with hydrophilic polymers such as polyacrylamide. If a plurality of channels are used, then the plurality can be arranged in an array when disposed near the surface of the gel.

In another embodiment of the invention, the apparatus described above should be able to extract proteins in 10 minutes when used for some applications, and under two minutes in other applications.

The invention also is directed to methods for extracting proteins from a gel by using the apparatuses disclosed herein. In one embodiment, one or more proteins are transferred out of a gel. The first end of a channel described above is secured adjacent to a gel. When an electric field is applied across the channel, proteins are extracted from the gel, and stack at the first end of the channel. The proteins are then transferred to the second end of the channel by stopping the electric field after the proteins have stacked in the first end of the channel, removing the first end from the gel, and transferring it into a reservoir of fresh electrolyte solution. The high electric field is then reapplied, so that the proteins are transferred to the second end of the channel. In another embodiment, instead of repositioning the first end of the channel from the gel to a reservoir after gel protein extraction, the first end can remain in contact with the gel for continuous protein extraction. At the same time, the extracted proteins are transferred to the second end of the channel under the influence of the electric field.

In another embodiment of the invention, the proteins are transferred from the first end to the second end of the channel by raising the channel slightly above the gel, and pressurizing the housing so that the proteins are transferred to the second end.

In yet another embodiment of the invention, the proteins are transferred from the first end to the second end of the channel, by raising the channel slightly above the gel, and applying negative pressure to the second end of the channel, so that the proteins are transferred to the second end.

In yet another embodiment of the invention, the transferred proteins are then sent directly to a micro membrane reactor containing proteolytic enzymes for digestion. The proteins could also be sent directly to a column reactor containing particles or beads with proteolytic enzymes immobilized on them for digestion. The channels themselves could also contain these particles or beads with immobilized proteolytic enzymes for digestion.

In another embodiment, the proteins to be transferred are subject to in-gel digestion. The digestion could also take place on membranes placed between the gel and the channel. The proteolytic enzymes could also be in solution inside the channel. These digested proteins could be transferred directly to a mass spectrometer from the first or second end of the channel. They could also be similarly directly transferred to a MALDI target plate for further analysis with a mass spectrometer.

In another embodiment of the invention, the enzyme used for digestion is trypsin. In another embodiment of the invention, the locations to place the channels are visualized. These locations can be visualized through the use of Coomassie blue, silver staining, or SYPRO fluorescent dyes.

DETAILED DESCRIPTION

The microfluidic apparatus of the present invention which is used to perform gel protein extractions allows the transfer of proteins directly from a gel to a fluidic channel by exploiting electrophoretic extraction. The invention harnesses electrophoretic forces to mobilize proteins from the gel and concentrate them in the fluidic channel tip. The small dimensions of fluidic channels not only allows the application of high electric voltages during electrophoretic extraction for rapid and quantitative protein transfer, but also offers the promise of providing the high resolution analysis of overlapping protein spots on gels. Furthermore, the presence of sample stacking and the absence of electroosmotic pumping (an electrically-driven pump originated from negatively charged silica surface for bulk solution movement) in the channel contribute to significant increase in protein concentration inside a narrow solution plug during protein extraction.

Figure 1:
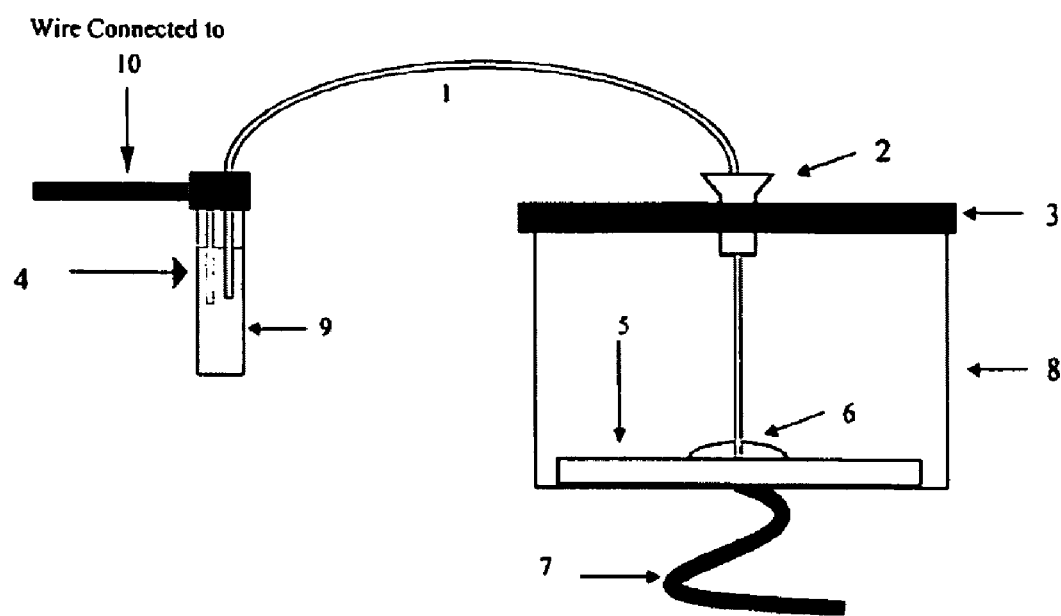
FIG. 1 schematically illustrates an example of a gel protein extraction apparatus.

The method of protein extraction is performed by using the apparatus of the present invention, as illustrated in FIG. 1. In this apparatus, a fluidic channel 1 is fed through a housing cover 3 and is held in position by a sleeve 2. The fluidic channel is held in place over a specific position on a gel 5. The gel may have undergone 1D or 2D gel electrophoresis. Once gel electrophoresis has been completed, the gel is washed, stained, and equilibrated, and then is placed in the apparatus housing 8 with electrical contact to a ground electrode 7. The fluidic channels are then placed over and put in contact with the desired spot on the gel, either by manual or robotic controls. An electric potential is then applied at the outlet reservoir 9 from a high voltage power supply 10 through an electrode 4. The resultant potential drop across the length of the fluidic channel, and subsequently at the fluidic channel-gel interface, and through the gel to the ground, provide a high electric field in the region of protein extraction.

Under this high electric field, SDS denatured proteins migrate into the fluidic channel. After a chosen extraction time, the potential is removed and the fluidic channel is repositioned to a reservoir filled with an electrolyte solution. The potential is then reapplied, and the protein band electrophoretically migrates through the fluidic channel and past an optional detector. In an alternate approach, the fluidic channel is slightly raised above the gel once the potential is initially removed, whereupon the gel chamber is pressurized. In this embodiment, the protein band is hydrodynamically mobilized past the detector. In another embodiment, instead of repositioning the first end of the channel from the gel to a reservoir after gel protein extraction, the first end can remain in contact with the gel for continuous protein extraction. At the same time, the extracted proteins are transferred to the second end of the channel under the influence of the electric field Additional embodiments of the apparatus and methods of the present invention include the use of micro membrane reactors for protein digestion, coupled with mass spectrometry for further analysis of the proteins. In such embodiments, the proteins can be either electrokinetically or hydrodynamically mobilized through a micro-membrane reactor where protein digestion occurs. The resultant peptides are mobilized through fluidic components and introduced into a mass spectrometer for further analysis. The protein analyte can then be identified using database searching of the peptide mass fingerprints from the resulting mass spectrum.

The speed and the effectiveness of protein electroelution are dependent on the potential drop and the electric field strength at the fluidic channel/gel interface. Thus, several important factors, including channel position relative to a gel, electrophoresis buffer concentration, channel dimensions, and gel thickness, are important for electronic protein transfer.

Furthermore, head column stacking in the present gel protein extraction apparatus is exploited for preconcentration of extracted protein analytes.

Basic Apparatus Elements

As illustrated in FIG. 1, the apparatus of the invention comprises a housing 8 overlaid with an apparatus cover 3, wherein the housing has disposed therein a gel 5 containing one or more proteins to be extracted and an electrolyte solution 6. A first end of the one or more fluidic channels 1 is passed through the cover and secured in fashion so that the one or more fluidic channels are positioned adjacent to a location on the gel disposed within the housing. The gel contains the protein materials to be extracted from the gel and transferred through the channels.

The apparatus also comprises one or more outlet reservoirs 9 having disposed therein an electrolyte solution, a first end of one or more outlet electrodes 4, and the second end of the one or more fluidic channels 1. A high voltage power supply is attached to the second end of the outlet electrodes for applying an electric field across the length of the one or more fluidic channels.

The housing 8 of the apparatus is constructed so as to be able to contain therein a gel 5 and an electrolyte solution 6. In one embodiment, the housing contains a ground electrode 7. In another embodiment, the housing can hold enough electrolyte solution 6 so that the gel 5 disposed within it would be submerged in the electrolyte solution. In yet another embodiment, the housing is air tight, so that with the appropriate cover 3, the inside of the housing could be pressurized.

The cover 3 of the apparatus is constructed to cover the gel 5 disposed within the housing, and to allow one or more fluidic channels 1 through the housing to be positioned on or near the gel within. The housing cover 3 includes one or more apertures, holes or ports with one or more sleeves 2 disposed therethrough. Each aperture, hole, or port has a single sleeve disposed therethrough. The sleeve can be constructed out of any suitable material, including polymers. The main function of this sleeve is to position the fluidic channel above the protein spot on the gel, while simultaneously disallowing penetration of the fluidic channel through the surface of the gel.

The channels 1 are thus disposed through the housing cover 3 through the sleeves 2. In one embodiment of the apparatus, there is a single channel disposed through a single sleeve in the housing cover. In another embodiment, the cover 3 has disposed therethrough a plurality of sleeves 2, each sleeve allowing a fluidic channel to pass therethrough. In such an embodiment, the fluidic channels could be arranged in an array which contacts the gel 5. The channels could be positioned sequentially at various gel locations using a manual or automated positioning system, enabling individual or groups of fluidic channels within the array to sequentially or simultaneously extract multiple proteins from the various locations using a single extraction apparatus.

The gel 5 disposed within the housing can be made out of any suitable material known to one skilled in the art. The gel can be either a pre-cast commercially available gel, or a gel cast in-house. Exemplary suitable gel materials include polyacrylamide and agarose. In one embodiment, the gel is a gradient gel with a range of about 4% to about 20% polyacrylamide. In another embodiment the gel is a Tris/Tricine SDS polyacrylamide gel. In yet another embodiment, the gel is one which had been used to perform 1D or 2D gel electrophoresis. Once gel electrophoresis has been completed, the gel is washed, stained, and equilibrated with electrophoresis buffer, and then placed in the apparatus housing 8 with electrical contact to a ground electrode 7.

The gels can also be a variety of thicknesses, preferably ranging between about 1 mm and about 100 µm thick. In one embodiment, the gels disposed within the housing can be ultra-thin-layer gels. Ultra-thin-layer SDS gel electrophoresis has been used in conjunction with automated fluorescence detection for rapid, high throughput, and high resolution analysis of proteins in the molecular mass range of 14–116 kDa (74, 75). The good heat dissipation inherent to the ultrathin (190 µm) format enables the use of agarose and agarose-based composite separation matrixes, which can be easily replaced within the separation platform. In addition to the rapid and high efficiency separations, the use of thinner gels may greatly facilitate the electronic protein transfer through the reductions in protein migration distance across the gel and the distance between grounding wire and channel extraction end (see FIG. 1). The electric field at the channel tip increases with decreasing electrode distance (72). By utilizing different spacers and combs, polyacrylamide gels with various thicknesses, including 1.0 mm, 0.75 mm, and 0.50 mm can be fabricated and employed.

The fluidic channel 1 of the apparatus is constructed to allow an electric potential to be created along its length for the purpose of extracting a protein from a gel 5. A fluidic channel is a passage, chamber, or conduit for transporting fluids. The channel can be of almost any length, and in one embodiment the channel is preferably between about 1 cm and about 50 cm long. The channel can also be a microscale fluidic channel. In another preferred embodiment, the channel is a capillary, even more preferably a fused silica capillary. In such an embodiment, the channel can have an inner diameter ranging between about 5 µm and about 100 µm and an outer diameter ranging between about 100 µm and about 500 µm. In another embodiment of the invention, the channel 1 is shaped in such a way, that the transferred proteins stack inside of it, and in some applications the transfer can take as little as two minutes. In other applications, the transfer can take as little as 10 minutes.

In another embodiment of the invention, one or more fluidic channels are joined with one or more fluidic holding channels. In this embodiment, one or more fluidic extraction channels containing an electrolyte solution have a first end disposed through the apparatus cover and are secured in place at the gel interface. The second end of the extraction fluidic channel joins with the first end of a fluidic holding channel containing an electrolyte solution. The second end of the one or more fluidic holding channel ends in one or more outlet reservoirs 9 containing an electrolyte solution and a first end of an outlet electrode 4. A high voltage power supply is attached to the second ends of the one or more outlet electrodes through an array of switches allowing one or more fluidic channels to be selected for extraction and not others.

The fluidic channels are positioned over desired locations on the gel, either via robotic or manual control. In some embodiments the desired location is directly over a spot on the gel where the protein to be extracted is located. In some embodiments, therefore, the proteins to be transferred need to be visualized. The visualization can be done using any one of a number of optically detectable elements known to one of skill in the art, including Coomassie blue, silver staining, or fluorescent dyes, more preferably SYPRO fluorescent dyes.

Accordingly in some embodiments, the proteins are visualized to ascertain where to place the extraction channels. The current protein loading limitation (50–100 ng/spot) on polyacrylamide gels for capillary extraction studies lies in the visualization of protein spots using Coomassie blue staining and is in good agreement with those (0.1–0.2 µg/spot) reported in the literature (76). To enhance the visualization of protein spots on gels, silver staining is a popular and more sensitive method with a detection limit between 1 and 10 ng (76). Despite its complicated and poorly defined binding mechanism, it is well known that silver has variable binding characteristics towards many proteins and a relatively low dynamic range (75). Many of the fixation techniques in silver staining, including the use of glutaraldehyde, can cross-link the proteins and prevent efficient off- or in-gel digestion by trypsin or other proteases (35,36,37). Furthermore, silver ions interfere with mass spectrometric analysis, including ESI-MS and MALDI-MS (35,36). Though glutaraldehyde can be omitted from silver stain formulations to improve compatibility with mass spectrometry, detection sensitivity is compromised. Peptide yields from solvent extractions of silver stained proteins are often lower than those obtained from coomassie blue-stained proteins unless extra laborious destaining and washing steps are included in the protocol (9,38).

A number of studies have demonstrated protein visualization on SDS-PAGE using fluorescent dyes (60,74,75,34, 37,39), in particular, SYPRO fluorescent dyes such as SYPRO Orange, SYPRO Red, and SYPRO Ruby are commercially available from Molecular Probes. Although the structures for these products are not in the public domain, it has been reported that SYPRO Ruby dye is a transition metal organic complex that binds directly to proteins by an electrostatic mechanism (40,41). SYPRO Orange and Red dyes are organic fluorophores that interact with proteins by intercalating into SDS micelles (60,41). Both probes are non-fluorescent in water but highly fluorescent in detergent, in which they take advantage of SDS binding to proteins (1.4 g of SDS/g of protein) to build a fluorescence-promoting environment. Comparison of SYPRO dyes with silver staining in SDS gels has shown that this class of fluorescent dyes detects polypeptides with sensitivity similar to that obtained by silver staining (60,34,37). Binding of the dyes to the protein is stoichiometric and fluorescence is related to the amount of dye binding, therefore, the dynamic range is three orders of magnitude greater than for silver staining (34). Moreover, it has been shown that proteins detected by SYPRO staining are compatible with MALDI-MS analysis (37,40). To enhance the visualization of protein spots with 1–100 ng protein loading, SYPRO dyes can be applied for postelectrophoretic staining of proteins separated by SDS-PAGE.

As discussed above, the fluidic channels 1 are disposed through the sleeves 2 in the housing cover 3 and are placed in their desired locations at the gel interface. A variety of substrate materials may be utilized to construct the channels. Typically, because the channels are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the fill range of conditions to which the channels may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. One preferred embodiment of the channel of the present invention includes a planar glass substrate. Additionally, it will often be desirable to provide an insulating coating or layer, e.g., silicon oxide, over the substrate material, and particularly in those applications where electric fields are to be applied to the device or its contents. Accordingly, in another preferred embodiment, the channel is coated with insulating layer.

In additional preferred aspects, the substrate materials will comprise polymeric materials, e.g., plastics, such as polymethylmethacrylate (PMMA), polycarbonate, polytetrafluoroethylene (TEFLON.TM.), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. In one preferred embodiment, the inner surface of the channel is coated with a hydrophilic polymer, including either polyacrylamide or agarose. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system.

In another embodiment the channel 1 is filled with an electrolyte solution. The electrolyte solution 6 is disposed around the channel 1 and the portion of the gel 5 where the channel is placed near. The electrolyte solution can contain a buffer, more preferably an electrophoresis buffer, or a salt. In one embodiment, the electrolyte solution contains Tris-HCl, up to a concentration of about 25 mM. The electrolyte solution can have a pH over a broad range of pH values, with a preferred pH ranging between 6 and 10, more preferably with a pH of about 6.8. In some embodiments, the electrolyte solution completely covers the gel disposed within the housing. In other embodiments, the electrolyte solution covers only the area of the gel around where the channel is placed on or near the gel.

The outlet reservoir 9 of the apparatus is a reservoir of electrolyte solution separate from the electrolyte solution 6 in the housing. In one embodiment, the outlet reservoir contains the first end of an outlet electrode 4. Additionally, the second end of the fluidic channel 1 is placed in the outlet reservoir. In another embodiment, the second ends of a plurality of fluidic channels are placed in the outlet reservoir. In yet another embodiment the second ends of a plurality of fluidic channels are placed in a plurality of outlet reservoirs, in a one to one ratio, so that each outlet reservoir contains one end of one channel.

The apparatus and methods of the present invention preferably employ electrokinetic transport systems for manipulating fluids and other materials within the microfluidic channel networks. As used herein, "electrokinetic material transport systems" include systems which transport and direct materials within an interconnected channel and/or chamber containing structure, through the application of electrical fields to the materials, thereby causing material movement through and among the channel and/or chambers, i.e., positively charged species will generally be attracted to the negative electrode, while negative ions will be attracted to the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., silanol groups in etched glass channels or glass microcapillaries, those groups can ionize. In the case of silanol functional groups, this ionization, e.g., at neutral pH, results in a negatively charged surface, creating a concentration of counterions such as cations at near the fluid/surface interface, or a positively charged sheath surrounding the bulk fluid in the channel. Application of a voltage gradient across the length of the channel, will cause the positively charged sheath to move in the direction of the voltage drop, i.e., toward the negative electrode. Although described as electrophoretic or electroosmotic, the material transport systems used in conjunction with the present invention could in some case rely upon a combination of electrophoretic and electroosmotic transporting forces to move materials.

The outlet electrode 4 of the apparatus is an electrode contained within the outlet reservoir. In one embodiment, this outlet electrode is made of any suitable materials, including metals, more preferably platinum or gold. In another embodiment, the outlet electrode can be a thin film of metal integrated into a variety of substrates, including glass or plastic. In another embodiment multiple outlet reservoirs 9 each contain one outlet electrode.

The power supply is electronically connected to the outlet electrode 4. In one embodiment, it is attached to the second end of the outlet electrode. In another embodiment, the power supply is capable of producing an electric field across the fluidic channel between about 100 V/cm and about 1000 V/cm. In another embodiment, the power supply is capable of being attached to multiple electrodes in multiple outlet reservoirs 9. In another embodiment, the power supply is capable of producing different electric field strengths along different fluidic channels 1 at the same time.

There is a continuous current drop during the extraction period. This current drop implies the depletion of electrolytes at the fluidic channel/gel interface and the generation of a low-conductivity solution plug at the extraction end of the channel. Thus, a higher voltage drop per channel length occurs across the small plug of low-conductivity buffer than that present in the rest of the fluidic channel. The presence of a higher electric field strength near the extraction end of the channel not only promotes the electroelution of SDS-protein complexes, but also offers sample stacking/ concentration as the result of field-amplification (13,14,15, 16). The complexes that enter the channel rapidly migrate to the front of the low-conductivity solution plug due to the presence of the higher electric field strength. At that point they encounter a lower electric field strength and slow down. The process literally stacks the extracted protein complexes at the front of the low-conductivity solution plug/ background electrolyte interface.

Both the outlet reservoir (see FIG. 1) and the channel can be filled with 20 mM Tris at pH 6.8. However, the same electrolyte solutions at lower concentrations are employed for establishing the electric contact between the gel and the grounding wire. Dependence of electrolyte depletion at the channel/gel solution interface on protein extraction can therefore be examined in different applications by lowering the electrolyte concentration at the interface. Nevertheless, the decrease in electrolyte concentration may affect the buffering capacity and the ability to maintain electric contact at the interface. Thus, head column stacking (71) can also be optimized for protein extraction and sample preconcentration, for different conditions by manipulating the electrolyte concentration.

In another embodiment of the invention, instead of using an electrophoresis buffer with lower concentrations at the channel/gel interface, the entire gel protein extraction apparatus is initially filled with 20 mM Tris at pH 6.8. Pressure injection of a plug of water will be performed prior to channel extraction. The presence of a water plug at the head of the channel creates a nonuniform electric field distribution across the channel upon the application of a positive electric voltage at the outlet reservoir for protein extraction and concentration. Assuming that length xL of the column is filled with water and length (1−x)L of the channel is filled with the background electrolyte, the local electric field strengths in the water plug, $E_W$, and in the rest of the capillary, $E_B$, are given by $$E_W = \gamma E_0 / [\gamma x + (1-x)] \quad (1)$$

$$E_B = E_0 / [\gamma x + (1-x)] \quad (2)$$

where $\gamma$ is the ratio of resistivities of water and 20 mM Tris and $E_0 = V/L$ is the field strength of a uniform system, whether it is water or 20 mM Tris. Although the absolute values of the electric field strength in these two regions will depend on x, the ratio between them as $\gamma$ ($E_W/E_B = \gamma$) will remain a constant (13,14,15,16).

In the absence of electroosmotic pumping inside the coated channels, the plug of water stays at the extraction end. A longer water plug may support an even larger amount of protein extraction (with longer extraction time) and greater protein preconcentration at the front of the water plug/background electrolyte interface. However, a shorter water plug allows the presence of a higher electric field strength at the extraction end for rapid and effective protein extraction. Thus, the combination of head column stacking with channel extraction of gel proteins can be optimized by considering the speed of protein transfer, the concentration of extracted protein, and the extent in the recovery of gel proteins. In addition, the introduction of the water plug reduces the average conductivity and the electric current across the capillary, allowing the application of even higher electric voltages at the outlet reservoir for further enhancement of electronic protein transfer.

The electric voltage applied, and therefore the resulting electric field strength across the channel, can be further increased by simply reducing the inner diameter of the channel without the negative joule heating effect. Example of fluidic channels which can be used are fused-silica capillaries with the dimensions of 50 μm. i.d./150 μm o.d., 25 μm i.d./150 μm o.d., and 10 μm i.d./150 μm o.d.

There are a variety of methods for transferring the proteins down the fluidic channel 1 from the first end towards the second end. In one embodiment, the high electric field can be turned off, and the first end of the fluidic channel can be removed from its location at the channel/gel interface and can be placed in a separate inlet reservoir that contains fresh electrolyte buffer. Once the first end of the fluidic channel is in the separate inlet reservoir, the electric field can be turned on again In another embodiment, instead of repositioning the first end of the channel from the gel to a reservoir after gel protein extraction, the first end can remain in contact with the gel for continuous protein extraction. At the same time, the extracted proteins are transferred to the second end of the channel under the influence of the electric field When the electric field is turned on again, the transferred proteins will migrate toward the second end of the fluidic channel. Another method to transfer proteins to the second end of the fluidic channel is by lifting the first end slightly above the gel, and applying positive pressure inside the housing, or negative pressure to the second end of the channel.

Modifications to Allow for Further Analysis of the Extracted Proteins

The protein which is extracted from the gel and transferred from a first end of a fluidic channel to a second end of the fluidic channel can further be analyzed by a variety of instruments adjacent to the channel, and/or be transferred to undergo mass spectroscopy or other studies. Modifications in the present apparatus allows for the direct analysis of peptides resulting from digested protein in the gel spot. These modifications allow digestion of the extracted proteins with or without sectioning of the gel. The extracted proteins, whether digested or not, can also be subjected to further analysis by mass spectrometry.

In some embodiments, the present apparatus can include an optical detection window disposed across one or more fluidic channels. Optical detection windows are typically transparent such that they are capable of transmitting an optical signal from the channel over which they are disposed. Optical detection windows may merely be a region of a transparent substrate containing fluidic channels or a transparent cover layer, e.g., where the cover layer is glass or quartz, or a transparent polymer material, e.g., PMMA, polycarbonate, etc. Alternatively, where opaque substrates are used in manufacturing the fluidic channels, transparent detection windows fabricated from the above materials may be separately manufactured into the channel.

In one embodiment of the invention, there can be a detector near one or more outlet reservoirs 9 for monitoring extracted proteins. In another embodiment there is a detector near one or more fluidic channels monitoring extracted proteins. In additional embodiments of the invention, the detector is a UV detector or a fluorescence detector.

In some embodiments of the invention, the proteins can be subject to digestion. In another embodiment, the proteins can be denatured in sodium dodecyl sulfate. In some embodiments, the proteins are subject to digestion before they are transferred to a fluidic channel 1. In these embodiments, the digestion of the proteins could occur in the gel 5. The proteins could be digested with a variety of suitable proteolytic enzymes, including trypsin. The digested proteins could then be fluidically transferred to a mass spectrometer from the first end of the fluidic channel. Alternately, they could also be transferred to a MALDI target plate for further analysis by a mass spectrometer. They could also be transferred from the second end of the fluidic channel.

In other embodiments, the proteins could be digested during their transfer through the fluidic channel 1. The proteins could undergo digestion in a membrane containing immobilized proteolytic enzymes positioned between the gel 5 and the first end of the fluidic channel. The proteolytic enzyme could be trypsin. The digested proteins could then be fluidically transferred to a mass spectrometer from the fluidic channel. They could also be transferred to a MALDI target plate for further analysis by a mass spectrometer.

Figure 2:
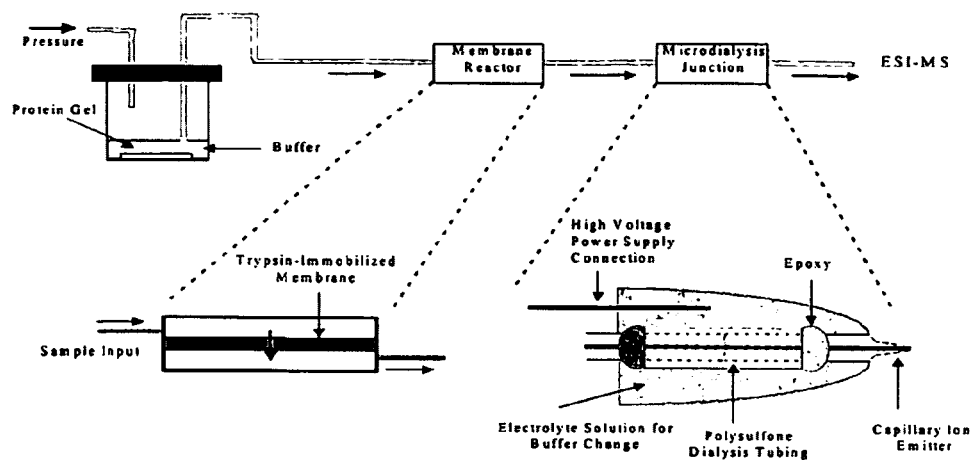
FIG. 2 schematically illustrates a component-level platform for rapid and sensitive identification of proteins resolved on polyacrylamide gels.

In another embodiment, the proteins are digested after transfer to the fluidic channel 1. As illustrated in FIG. 2, the proteins could be transferred from the fluidic channel to a micro membrane reactor containing proteolytic enzymes for digestion. The fluidic channels could also contain particles or beads with immobilized proteolytic enzymes on their surface. The proteolytic enzyme could be trypsin. The digested proteins could then be fluidically transferred to a mass spectrometer from the first end of the fluidic channel. They could also be transferred to a MALDI target plate for further analysis by a mass spectrometer. They could also be transferred from the second end of the fluidic channel.

Parameters of One Specific Embodiment of the Apparatus of the Invention

One embodiment of the gel protein capillary extraction apparatus of the invention (see FIG. 1) has been developed for rapidly and effectively transferring protein analytes from polyacrylamide gel to fused-silica capillary. The fused-silica capillaries (50 μm i.d./192 μm o.d.) are internally coated with polyacrylamide (61, 62, 63) for the elimination of electroosmotic flow and protein adsorption onto the capillary wall. Both the outlet reservoir and the capillary are filled with electrophoresis buffer of 20 mM Tris at pH 6.8. A positive electric voltage of 7.4 kV is applied at the outlet reservoir through a platinum electrode and generates an electric field strength of 200 V/cm over a 37-cm total capillary length. The gel in contact with the electrophoresis buffer is connected to a common ground. A UV detector is placed near the outlet reservoir (7 cm to the end of the capillary) for monitoring the transferred proteins.

Precasted gradient gels (4–20% total monomer concentration) are employed in this study and the proteins resolved on the gradient gels are visualized using coomassie blue staining. Each gel is rinsed in water and washed two times with 10% SDS for a total of 40 minutes. The gels are rinsed again with water and equilibrated with 20 mM Tris at pH 6.8 Finally, each gel containing the resolved and stained proteins is placed in our gel protein capillary extraction apparatus for mechanistic studies of electronic protein transfer.

The electric current, measured by the current-monitoring method (64), continuously decreases from 9 μA to 6 μA during the two minutes of the protein extraction process. This continuous current drop indicates the depletion of limited electrolytes near the end of the capillary during the extraction period. In addition, the extracted protein analytes are present in the low conductivity zone containing depleted electrolytes which contribute to fieldamplification and sample stacking/concentration (13,14,15,16). After the 2-minute protein extraction, the high-voltage power supply is turned off and the end of the capillary facing the gel is lifted and placed in an inlet reservoir containing electrophoresis buffer. The platinum electrode in the inlet reservoir is connected to a common ground. Once the positive electric voltage is applied again at the outlet reservoir, the current is restored to 9 μA and the negatively charged SDS-protein complexes electrophoretically migrate toward the anodic end at the outlet reservoir. In another embodiment, instead of repositioning the first end of the channel from the gel to a reservoir after gel protein extraction, the first end can remain in contact with the gel for continuous protein extraction. At the same time, the extracted proteins are transferred to the second end of the channel under the influence of the electric field.

Advantages of the Apparatus of the Present Invention

The herein described high-voltage electronic transfer of proteins can be at least two orders of magnitude faster than the conventional electroelution and membrane electroblotting processes which takes 3–18 hours to complete (59,65, 66,67). A key to such rapid and effective protein transfer includes the use of small dimension fluidic channels (e.g., 50 μm i.d./192 μm o.d.) in physical contact with the gel, which provides a large potential drop and high electric field strength at the capillary/gel interface. The electroelution of proteins from SDS-PAGE to a membrane preconcentration cartridge within 2 hours has been reported (68). The Teflon tubing, which encases a polymeric preconcentration membrane, exhibits an i.d. of at least 400 µm (68, 69). Similarly, it takes 4 hours to electrophoretically elute the digested peptides from polyacrylamide gel to a cation exchange cartridge through a 1,500-µm-i.d. channel by Timperman and Aebersold (70). Another key factor contributing to the success of our electronic protein transfer technique involves the use of the large, negative electrophoretic mobilities of SDS-protein complexes in the electrophoresis buffer (20 mM Tris at pH 6.8). In contrast, acidic electrolytes, including the solutions of 20 mM ammonium acetate/1% acetic acid (pH 4.5) and 0.05% trifluoroacetic acid/10% acetonitrile, are utilized by Clarke (68) and Timperman (70) for positively charging the analytes.

The electric field at the extraction end is approximately inversely proportional to the outer radius of the channel. In one embodiment, The outer diameter of a capillary is etched down using the same procedure for the fabrication of nanoelectrospray emitters (73). Briefly, the polyimide coating on the outer capillary surface is removed, followed by etching the end of the capillary in a 30% hydrofluoric acid solution. A nitrogen flow is introduced into the capillary to prevent hydrofluoric acid from etching the inner capillary wall and the inner polyacrylamide coating. The extent of etching is determined by the etching time, typically around 20 minutes to 1 hour.

The technique harnesses electrophoretic forces to mobilize proteins from the gel and concentrate them in the capillary tip. The small dimensions of fused-silica capillaries not only allow the application of high electric voltages during electrophoretic extraction for rapid and quantitative protein transfer, but also offer the promise of providing the high resolution analysis of overlapping protein spots on polyacrylamide gels. Furthermore, the presence of sample stacking (13,14,15,16) and the absence of electroosmotic pumping (an electrically-driven pump originated from negatively charged silica surface for bulk solution movement) in the coated capillary contribute to significant increase in protein concentration inside a narrow solution plug during protein extraction Use of the Apparatus of the Present Invention in Conjunction with Mass Spectrometry The methods and the instruments of the present invention developed for performing electronic protein transfer can be utilized in conjunction with a mass spectrometer for further analysis of the extracted proteins. When used in conjunction with mass spectrometry, the apparatus of the present invention can be equipped with laser-induced fluorescence detection (LIFD) and/or a µ-trypsin membrane reactor. These bioanalytical tools will provide much greater speed, throughput, and sensitivity for linking 2-D PAGE with mass spectrometric analysis than existing technology. These tools are particularly useful for the study of organisms having fully sequenced genomes, and will both identify proteins (and their modifications in many cases) as well as provide quantitative measurements of expression levels. The ability to rapidly monitor a large array of proteins will allow cancerous cells to be distinguished from normal cells at the molecular level and enable the system level understanding of the complex molecular events and interactions underlying the development of cancers.

Integration of Gel Protein Extraction Fluidic Channels with µ-Trypsin Membrane Reactor and Mass Spectrometry As illustrated in FIG. 2, in some embodiments, the present apparatus can combine a fluidic channel gel protein extraction apparatus with a newly developed µ-trypsin membrane reactor (23), a microdialysis junction, and ESI-MS. Such an apparatus provides an integrated platform for rapid digestion of extracted protein and sensitive identification of protein digest using peptide mass mapping, (18) or MS/MS of peptide fragments (19,20,21,22). The integrated system together with an ion trap mass spectrometer allows direct identification of proteins separated on polyacrylamide gels in an automated and on-line format while minimizing sample loss and analyte dilution. When electronic protein transfer and LIFD detection of extracted SDS-protein complexes are complete, the applied voltage will be turned off. The extraction end of the capillary is connected to a pressure source (see FIG. 2), or to a Harvard syringe pump using an Upchurch capillary fitting, for introducing extracted proteins into a µ-trypsin membrane reactor. The protein digest can then be directly analyzed using ESI-MS.

The miniaturized trypsin membrane reactor, which can be placed within the fluidic channel of the apparatus, is constructed by first fabricating microfluidic channels on polydimethylsiloxane (PDMS) substrates. Capillary molding can be employed for the fabrication of the PDMS microchannels. A symmetrically configured membrane reactor, consisting of two aluminum plates, two glass slides, one polyvinylidene fluoride (PVDF) membrane immobilized with trypsin, and two PDMS substrates containing the microchannels and the capillaries can be assembled.

The porous structure of the PVDF membrane provides a large internal surface area (200 $cm^2$ of internal surface per $cm^2$ of frontal surface) for protein immobilization. The measured immobilization capacity for trypsin is around 200 $pg/cm^2$ of frontal surface and is in good agreement with those reported by the manufacturer for insulin and goat IgG, ranging from 85 $\mu g/cm^2$ to 294 $\mu g/cm^2$. The extent of protein digestion inside the membrane reactor can be controlled by various factors including the protein residence time, the protein concentration, the reaction temperature, and the membrane pore diameter. The ability to alter the digestion time by changing the flow rate provides a powerful means to control experimental conditions, making it possible to achieve the desired degree of digestion or to compensate for trypsin activity loss by decreasing the flow rate.

The immobilized trypsin molecules are resistant to high concentrations of denaturing reagents and organic solvent, including 4 M urea, 2 M guanidine-HCl, and 40% acetonitrile. The presence of SDS in the SDS-protein complexes does not interfere with proteolytic digestion and still results in complete cytochrome C sequence coverage using a µ-trypsin membrane reactor. The use of a microdialysis junction, containing a typical solution of 50% methanol, 49% water, and 1% acetic acid (v/v/v) at pH 2.6, not only provides the electrical connection for inducing electrospray, but also offers buffer exchange with limited analyte dilution for enhancing the protonation and the ionization efficiency of digested peptides. The presence of SDS in the SDS-protein complexes provides the negative electrophoretic mobilities at pH employed during electronic protein transfer. The SDS detergents are also utilized to enhance the solubility of the proteins and will be removed or reduced in the microdialysis junction prior to ESI-MS analysis of digested peptides.

Integrated Microfluidic Protein Gel Extraction Platform

Figure 4:
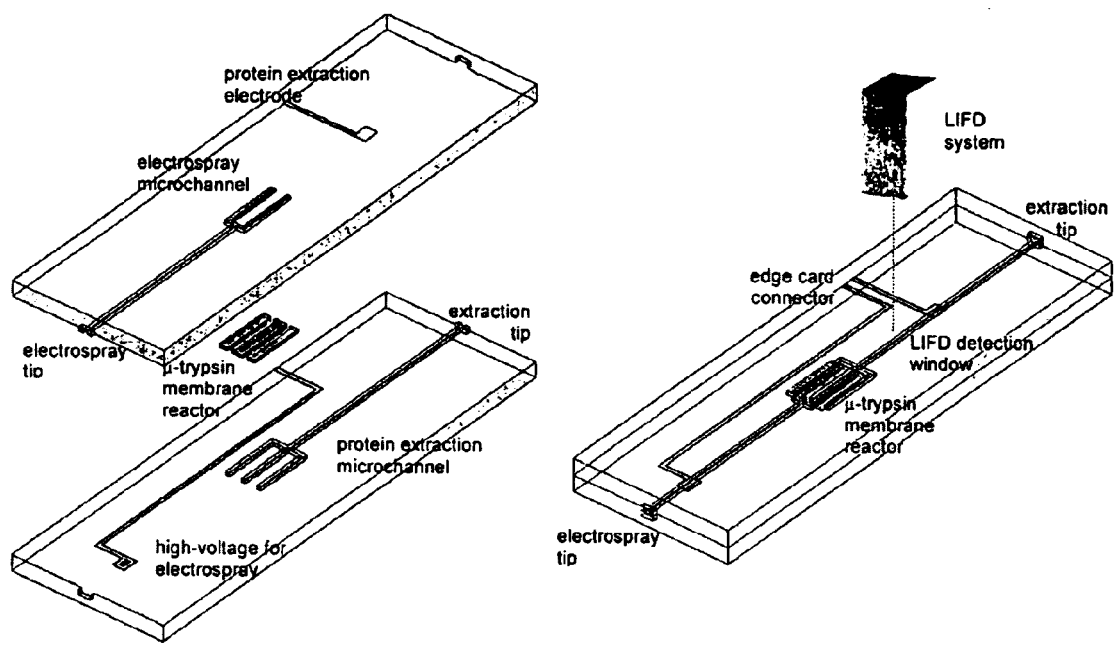
FIG. 4 illustrates (a) exploded view of a gPEP cartridge, and (b) assembled cartridge including laser-induced fluorescence detection system (drawings not to scale).

Another embodiment of the present invention, illustrated in FIG. 4, is a cartridge-based extraction system, termed Gel Protein Extraction Platform (gPEP). gPEP uses plastic microfluidic technology to integrate the full functionality required for protein extraction, LIFD, trypsin digestion, and electrospray sample dispensing for ESI-MS or MALDI-MS analysis. This prototype device is designed as a multiple-use, disposable extraction tool for providing an interface between 2-D PAGE and ESI-MS or MALDI-MS for the automated extraction and identification of extremely low-abundance proteins. The cartridge is fabricated using a combination of technologies including silicon micromachining, temperature-controlled plastic embossing, plastic metalization, and plastic-plastic thermal bonding. A schematic of the basic gPEP system is shown in FIG. 4. The assembled system in FIG. 4(b) shows the integration of a LIFD system for protein detection prior to proteolytic digestion in the µ-trypsin membrane reactor.

A microchannel for protein extraction exits the bottom surface of the cartridge. In one embodiment, a small extrusion is formed at the exit point. The extrusion is optional, and is not used in all embodiments of the gPEP system. When used, the extrusion dimensions will be in the range of about 20–500 µm in length with an inner diameter in the range of about 10–500 µm. The channel opening is positioned on the gel protein "spot" of interest. The extrusion, when used, helps to ensure sufficient contact between the gel and microchannel, while preventing the cartridge body from touching other parts of the gel which could lead to contamination.

An electrode embedded within the cartridge near the tip of the extraction channel provides high-voltage biasing of buffer solution within the channel to generate the desired electric field at the tip, initiating the extraction of protein from the gel. This electrode can be formed by integrating thin or thick conductive films directly into the plastic substrate, or by making electrical contact using an external electrode positioned in a fluid reservoir containing a solution in electrical contact with fluid in the extraction channel. After concentrating the extracted proteins within the microchannel, a pressure-driven pump is attached to the inlet, moving the sample further into the extraction channel. Alternately, the proteins can be mobilized using electrokinetic methods. The extracted proteins can be digested by forcing the solution through an integrated µ-trypsin membrane reactor positioned at the terminal end of the first microchannel, with the resulting peptides mobilized down a second microchannel on the opposite side of the membrane reactor, where they are expelled from the cartridge using electrospray dispensing (30,31). Alternately, the proteins can be digested by trypsin or similar enzymes in solution within the extraction microchannel. Alternately, they may be digested prior to entering the extraction tip using a trypsin membrane positioned between the gel and extraction tip. Alternately, they may be digested using trypsin immobilized on beads, on posts, or in a gel located within the microchannel.

The high voltage at the channel exit needed for electrospray is generated by a second electrode in contact with the microchannel near the exit point, fabricated using the same techniques described for integration of the extraction electrode. Other techniques for dispensing the solution from the spray tip are also applicable, such as employing a pressure pulse for mechanical spray, or dispensing by forming a droplet at the spray tip followed by contacting the droplet with an external surface to transfer the fluid to the external surface. The sprayed solution may be directed into individual wells of a titer plate for MALDI-MS analysis, or directly to ESI-MS as desired. Alternately, after digestion, the peptides may be returned through the extraction channel and dispensed from the same orifice used for extraction. This last embodiment offers the benefit of requiring only a single electrode for both extraction and electrospray, and a single microchannel and tip opening for extraction and spraying.

Polyearbonate (PC) or similar plastic material is used to form the plastic body of the gPEP cartridge. Polycarbonate's favorable mechanical properties, high melting temperature, suitability for micromachining via hot embossing, relatively low electroosmotic flow, and demonstrated adhesion with evaporated metal films make it a suitable substrate material. While there are many potential embodiments for the gPEP system, by combining permutations of the various alternatives presented above, two specific embodiments of the gPEP system are described here for illustration. In one embodiment, the cartridge is formed from two plates of PC, with the first plate housing the extraction microchannel, and the second plate housing the ESI microchannel and the µ-trypsin reactor membrane. The microchannels are designed so that all flow between the output of the extraction channel and the input of the ESI channel must pass through the µ-trypsin membrane reactor. Metalization and metal patterning via evaporation/sputtering, photolithography and chemical etching is performed after hot embossing to form electrodes for protein extraction and electrospray dispensing, with the metal films terminating at the cartridge edge for external connections.

As shown in FIG. 4, extraction microchannels which branch out at the µ-trypsin membrane reactor enhance the surface area for digestion. A trypsin-immobilized membrane is cut into 150 µm-wide strips and inserted into slots in the lower plastic plate formed during the initial hot embossing process. Another technique which can be used for protein immobilization is the use of a UV-curable hydrophobic polymer with sub-micron pore size. Such a polymer is selectively patterned within the microchannels after sealing the cartridge, and a trypsin solution flowed through the channels to impregnate the polymer through hydrophobic interactions.

The second embodiment is also formed from two plates of PC. The first plate contains a single microchannel for protein extraction and electrospray, and the first or second plate contains one or more reservoirs for fluidic access to the microchannel. Trypsin is added to the electrolytic solution within the microchannel, allowing in-solution digestion of the extracted proteins. After preparing the solution within the microchannel, proteins are extracted from the end of the microchannel which terminates at the side of the cartridge, with the high voltage required for extraction provided by an integrated or external electrode as described previously. After extraction, the proteins are digested by the trypsin in-solution, followed by dispensing of the resulting peptides from the extraction tip.

In general, dispensing may be performed using electrospray, pressure dispensing, contact dispensing, or related methods. While the present invention may employ any of these methods, electrospray dispensing offer the advantages of being relatively simple and requiring minimal external instrumentation.

The proposed approach to integrated electrospray dispensing is similar to a microchannel ESI device demonstrated by Ramsey's group (32). In their work, difficulties with effective ionization were experienced due to the flat tip geometry, leading to excessive band-broadening and sample dilution. An approach to avoid this problem was demonstrated by Oleschuk and Harrison (33), by milling a small hole at the microchannel exit and inserting a fused silica capillary into the hole to serve as the ESI tip. In our approach, a small protrusion is formed in the cartridge sidewall surrounding the electrospray tip using a hot embossing technique. The tip is created using a micromachined mold, which can be formed by silicon micromachining, microwire electrodischarge machining, or a similar method. The mold structure contains a central post which, when inserted into the microchannel opening, provides self-alignment between the embossing mold and microfluidic cartridge. The cartridge is assembled by aligning the plates and sealing the microchannels, ideally using thermally-activated direct-plastic bonding. Mechanical clamping and epoxy may also be used.

Alignment Between Extraction Cartridges and Gel

Ultimately, one or more extraction tips may be positioned at the desired gel protein spots using an automatic robotic system. In addition, a system is needed to allow convenient electrical and optical interconnects to the cartridge, where a cartridge is meant to describe a single element containing one or more individual protein extraction elements. A cartridge handling instrument which securely holds a cartridge, provides external electrical interconnection for the application of extraction and electrospray voltages, and applies pressure to the extraction tip as required to drive the extracted protein sample through the μ-trypsin membrane reactor. The instrument may also include optical interconnects to allow LIFD detection as depicted in FIG. 4. The handling instrument is designed to allow cartridges to be readily removed and replaced as needed in an actual laboratory environment.

In one configuration, one or more cartridges are positioned over the gel, with the position of each cartridge controlled by an individual positioning stage. Alternately, one or more cartridges may be located within a fixed frame, and the entire frame positioned over the gel to extract through selected cartridges, with the frame repositioned over the gel as required. Alternately, the cartridges may be repositioned relative to the frame, and the frame controlled by translational and/or rotational stages to provide additional flexibility in positioning the cartridges over the desired gel spots. In another configuration, the gel may be pre-cut using an existing robotic gel cutting system, with the cut gel sections placed in a frame so that the fixed location of each gel section is known, for example in a planar grid with equal spacing between rows and columns of gel sections. One or more extraction cartridges placed in a second frame, with each cartridge fixed in the frame with the same spacing as the gel sections, is then placed over the gel frame for extraction. Since the positions of the gel sections and extraction cartridges are predetermined, no robotic alignment is required in this configuration.

The invention will be further described in the following examples, which do not limit the scope of the invention described in the claims. The following examples illustrate various embodiments and uses of the apparatus of the present invention.

EXAMPLES

Example 1

Figure 3:
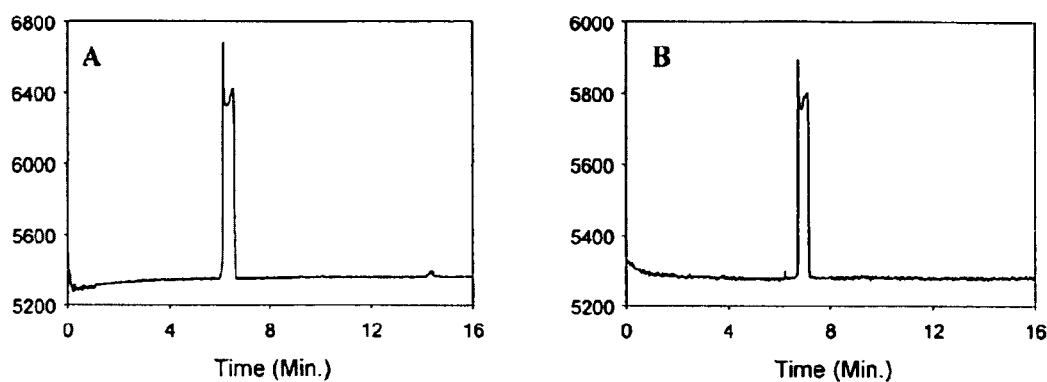
FIG. 3 illustrates Electropherograms of (A) electrokinetically injected SDS-cytochrome C complex in CZE with a concentration of 0.5 mg/ml and (B) extracted SDS-cytochrome C complex from SDS-PAGE with a protein loading of 100 ng.

As shown in FIG. 3, a protein loading of 100 ng of SDS-cytochrome C complex is extracted from polyacrylamide gel and monitored by UV absorbance at 280 nm. The results are compared with capillary zone electrophoresis (CZE) of protein sample containing SDS-cytochrome C complex with a concentration of 0.5 mg/ml. Thus, the concentration of extracted SDS-cytochrome C complex is estimated to be around 0.25 mg/ml inside a solution plug of 50–100 nL. The migration time of extracted cytochrome C complex to reach the UV detector is approximately 7.4 minutes and slightly longer than that obtained from CZE. UV absorbance detection scarcely reveals the presence of coomassie blue at 280 nm, while at 214 nm a broad peak is noticed prior to protein complexes.

Based on our estimations regarding the concentration (0.25 mg/ml) and the volume (50–100 nL) of extracted cytochrome C complex, approximately 12.5–25% of cytochrome C from a protein loading of 100 ng is recovered within 2 minutes of electronic protein transfer. The degree of recovery can be increased by increasing the extraction time. This is evidenced by the increase in protein peak width with increasing extraction time.

Example 2

Figure 5:
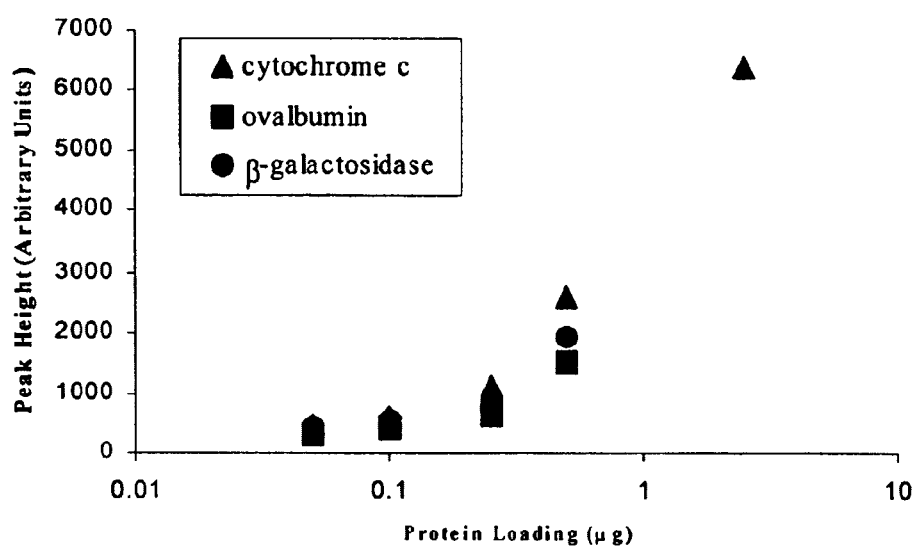
FIG. 5 is a graph illustrating the dependence of peak heights of extracted proteins upon protein mass loadings.

The results summarized in FIG. 5 further demonstrate the ability to rapidly transfer the SDS-cytochrome C complex over a wide range of protein loading, from 5 μg to 50 ng. Peak height of extracted protein complexes decreases with decreasing protein loading on polyacrylamide gel. However, the extent of decrease in peak height is reduced at low protein loadings as the size of a protein spot shrinks with decreased protein loading. The results also demonstrate the ability to extract higher molecular weight proteins such as ovalbumin and β-galactosidase with molecular mass around 45 and 116 kDa, respectively. The peak heights of extracted ovalbumin and β-galactosidase from a gradient gel are about half of those measured from cytochrome C at various protein loadings. However, the UV absorbance of denatured cytochrome C measured at 280 nm is two and four times of those obtained from β-galactosidase and ovalbumin at the same weight concentration, respectively.

Example 3

Figure 6A:
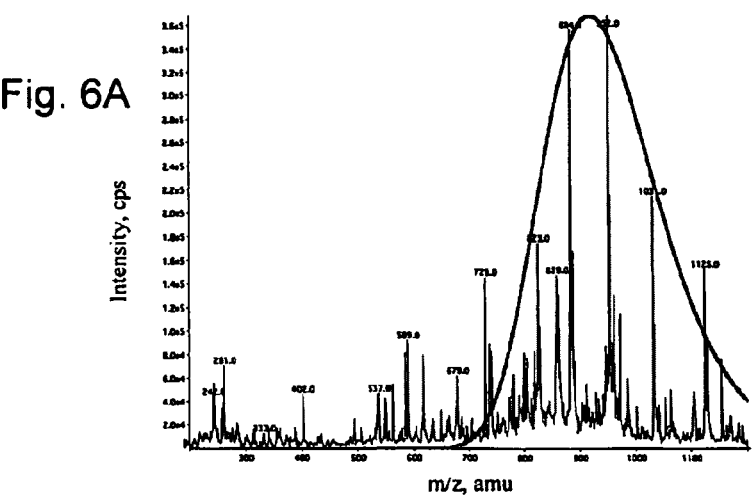
FIGS. 6A–6C are graphs illustrating flow rate dependence of trypsin digestion in a PVDF membrane with a pore diameter of 0.45 µm: (A) 0.3 µl/min, (B) 0.2 µml/min, and (C) 0.1 µl/min.
Figure 6B:
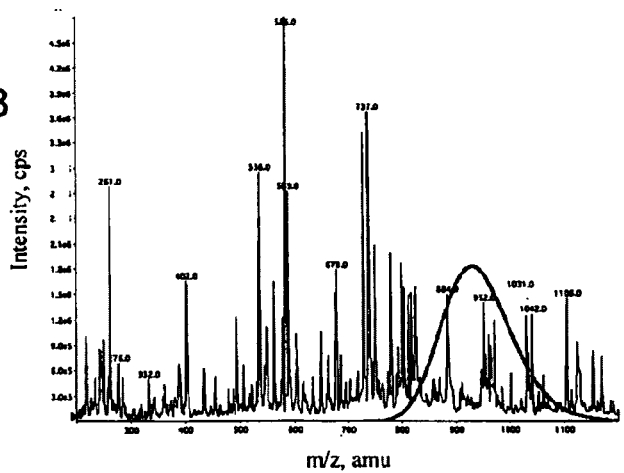
Figure 6C:
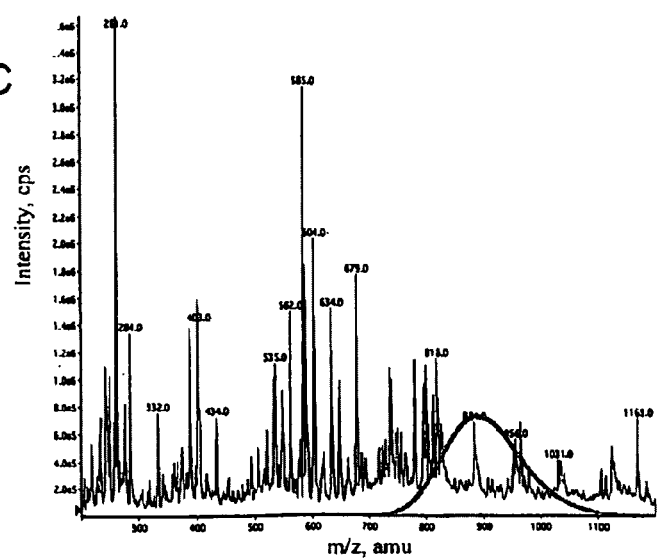

Denatured and reconstituted cytochrome C at a concentration of 1 mg/ml is introduced into a μ-trypsin membrane reactor at sample flow rates of 0.3, 0.2, and 0.1 μl/min. The corresponding digestion times inside the membrane reactor are 3, 5, 10 minutes, respectively. At room temperature, various degrees of the cytochrome C digestion are observed from partial digestion at 0.3 μl/min to near complete digestion at 0.1 μl/min (see FIGS. 6A, 6B and 6C). Presence of the cytochrome C envelope is quite obvious at a flow rate of 0.3 μl/min. In comparison with solution-based trypsin digestion, the membrane digestion is at least 500–1000 times faster than solution digestion and exhibits the advantage of avoiding autolytic interference from the proteolytic enzyme in the mass spectra.

Figure 7A:
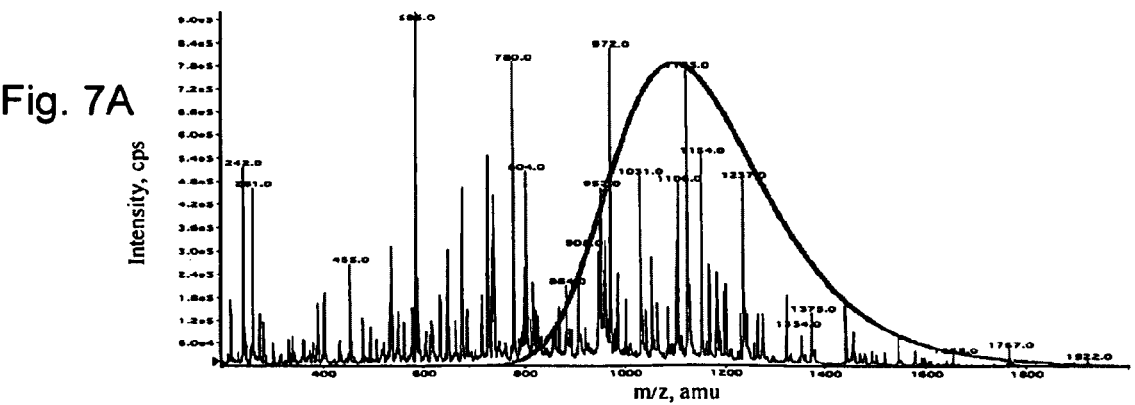
FIGS. 7A and 7B are graphs illustrating reaction temperature dependence of trypsin digestion in a PVDF membrane at a sample flow rate of 0.3 µl/min: (A) 40° C. and (B) 50° C.
Figure 7B:
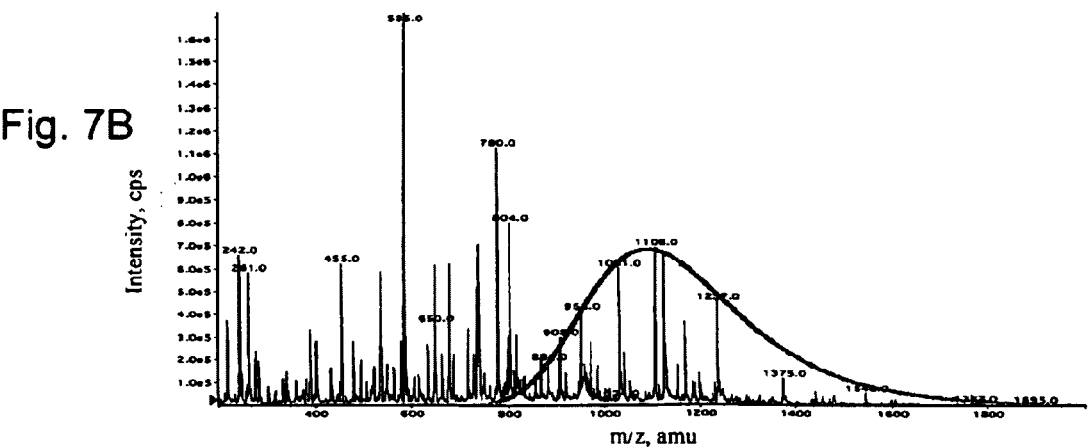

To investigate the effect of reaction temperature on protei digestion, the membrane reactor is placed on top of a hot plate. The ambient temperature surrounding the membrane reactor is increased to 40 and 50° C. while the sample folow rate is held constant at 0.3 μl/min. By comparing the results shown in FIGS. 6A, 7A and 7B, the number of identified peptide peaks and the degree of cytochrome C digestion at a concentration of 1 mg/ml clearly increase with increasing reaction temperature.

Figure 8A:
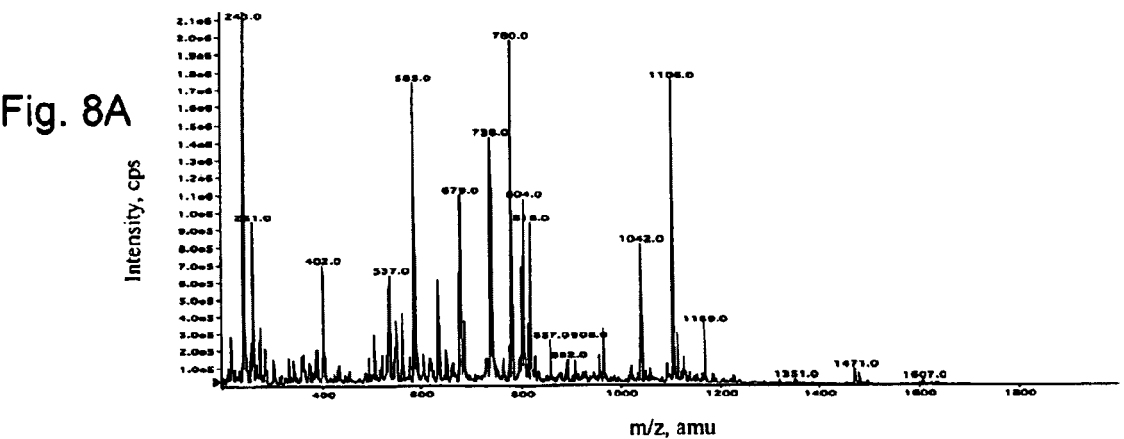
FIGS. 8A and 8B are graphs illustrating protein dependence of trypsin digestion in a PVDF membrane at room temperature and a sample flow rate of 0.3 µl/min: (A) 0.1 mg/ml and (B) 10 mg/ml.
Figure 8B:
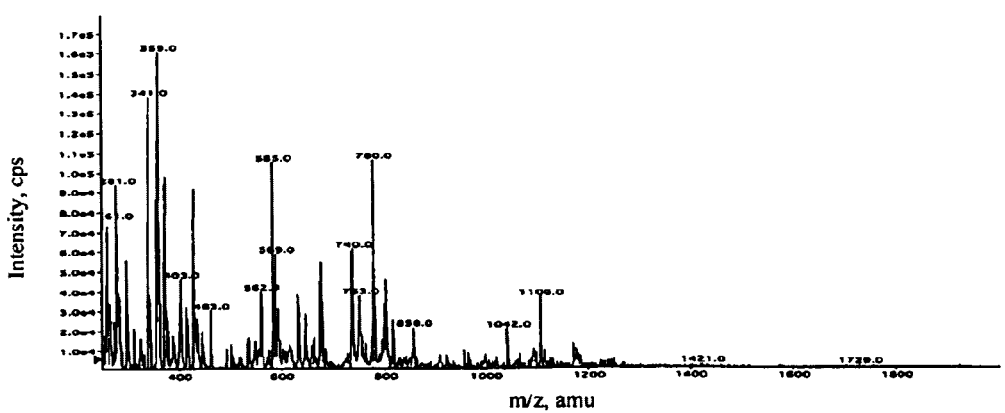

The extent of protein digestion at room temperature increases significantly by reducing the cytochrome C concentration from 1 mg/ml (see FIG. 6A) to 0.1 mg/ml (see FIG. 8A), and even further to 10 μg/ml (see FIG. 8B) at a sample flow rate of 0.3 μl/min. In fact, complete coverage of the cytochrome C peptides at a concentration of 10 μg/ml can be achieved at a flow rate as high as 1.5 μl/min, corresponding to a digestion time of only 36 seconds. By simply reducing the membrane pore diameter from 0.45 μm to 0.1 μm, the total membrane surface area available for trypsin immobilization and the immobilization capacity for trypsin are increased by a factor of four. Based on the extremely high local trypsin concentration inside the membrane reactor, complete digestion of cytochrome C at a concentration of 1 mg/ml is achieved at a sample flow rate as high as 1.0 μl/min. Due to a thicker membrane (180 μm thickness for the PVDF membrane with a pore diameter of 0.1 μm), this flow rate corresponds to a digestion time of 75 seconds at room temperature. The narrow pore diameter in the submicron range not only exhibits large surface area to volume ratio for protein immobilization, but also eliminates the constraints of diffusion-limited reaction kinetics.

Example 4

Figure 9:
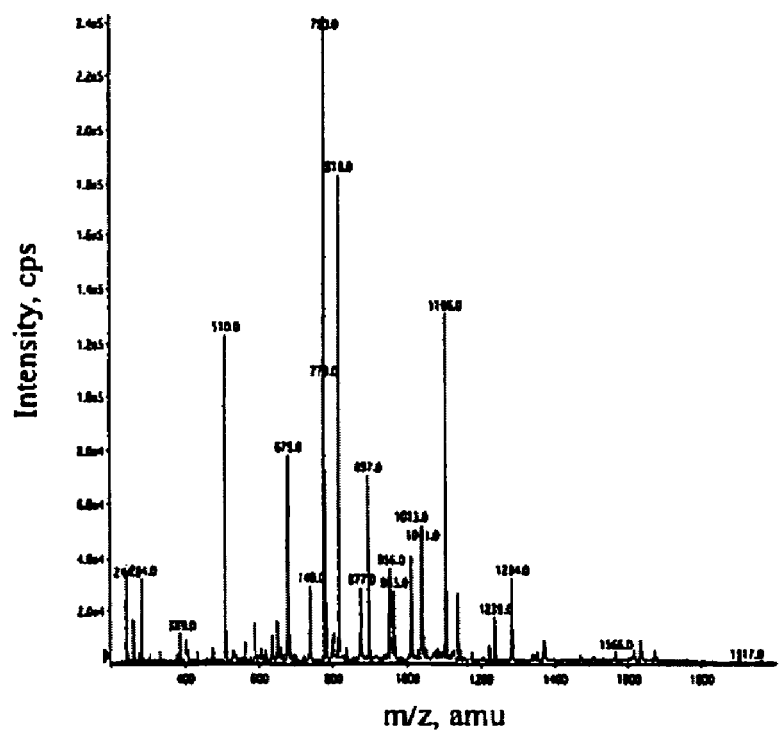
FIG. 9 is a graph of the positive ESI mass spectrum of extracted and digested cytochrome C peptides.

Our results (see FIG. 9) illustrate the promise of an integrated platform for rapid and sensitive identification of proteins resolved on polyacrylamide gels. The gel protein capillary extraction apparatus was connected to a Harvard syringe pump after capillary extraction of SDS-cytochrome C complex from a protein loading of 100 ng was complete (see FIG. 2). The protein complex was introduced into a μ-trypsin membrane reactor at a flow rate of 0.1 μl/min. The ESI mass spectrum demonstrates complete coverage of cytochrome C peptides.

Example 5

The gel protein extraction apparatus of the present invention can be used for many purposes, including analyzing the number of proteins which can be identified in a given genome and identifying low abundance proteins. As an example, the cell lysates from the yeast *Saccharomyces Cerevisia* can be analyzed with the gel protein extraction protein platform coupled with the μ-trypsin membrane reactor for linking 2-D PAGE with MS. In such an exemplary analysis, yeast cytosol will be prepared by suspending late-log phase *Saccharomyces cerevisiae* in the buffer containing 10 mM Tris (pH 8), 150 mM KCl, 1 mM $MgCl_2$, and 100 mM DTT. The solution will be passed through a chilled French press cell three times. Cell debris is removed by centrifugation, and cytosol is produced by ultracentrifugation. Aliquots are frozen in liquid nitrogen and stored at $-80°$ C. Prior to usage, thawed cytosol is denatured and reduced in a solution containing 8 M urea, 100 mM DTT, and 0.1 M Tris-HCl (pH 8.0). The protein solution is kept under a nitrogen atmosphere for 4 hours at room temperature. The denatured and reduced proteins are desalted using a PD-10 column.

2-D PAGE is then performed on the proteins. The combination of various ampholytes are employed for the formation of both narrow and wide pH gradients for isoelectric focusing separation. For separating proteins from cell lysates with broadly different pIs (see FIG. 10), a wide-range ampholyte blend will be selected, e.g. the combination of pharmalyte 3–5, 5–8, and 8–11.

Figure 10:
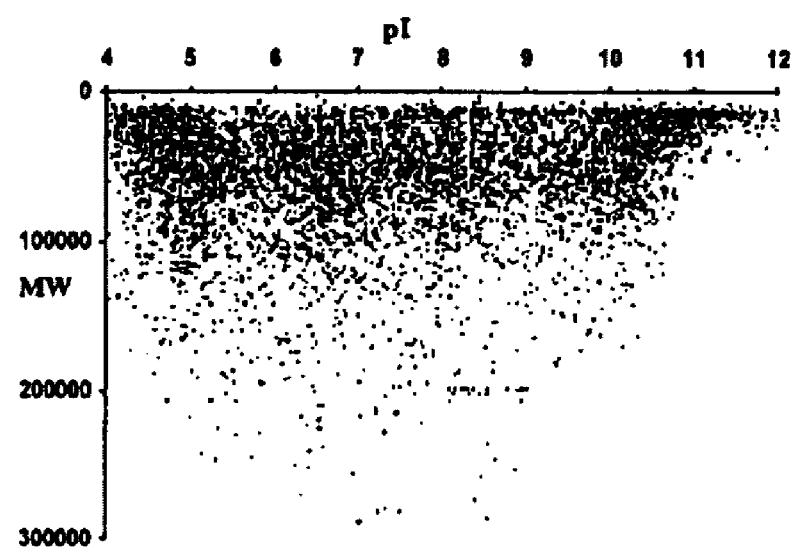
FIG. 10 is a graph of projected protein molecular weights and isoelectric points for *Saccharomyces cerevisiae*.

As shown in FIG. 10, the predicted pI distribution of proteins from *Saccharomyces cerevisiae* is ranged between pH 4 and pH 12. Thus, very basic proteins with pIs equal to or greater than 11 may not be resolved or could be lost to the catholyte using the currently available carrier ampholytes. In situations where enhanced resolution of proteins with similar pI values is desired, the use of narrow range ampholyte mixtures may be employed. Narrow range ampholyte mixtures generating gradients spanning 1 to 3 pH units are available from many commercial sources. However, our experience with this approach to high resolution isoelectric focusing separation has been somewhat disappointing, perhaps due to the limited number of ampholyte species in narrow-range "cuts". One solution is to blend narrow range ampholytes from several manufacturers.

In addition to being used for examining the number of yeast proteins which can be identified, the gel protein extraction apparatus coupled with the μ-trypsin membrane reactor for linking 2-D PAGE with MS, can also be used for the identification of low abundant proteins. Furthermore, "differential display" of proteomes for the comparisons of protein expression can be analyzed by studying the yeast culture under normal and stress conditions (29). Computer based methods for displaying protein distribution and relative protein expression rates measured by the Bio-Rad Fluor-S Multilmager System and LIFD can be established. Accordingly, the present apparatus and methods can be used to identify the dynamic range and the detection limit of yeast proteins.

LITERATURE CITED

1. Persidis, A., "Proteomics: An Ambitious Drug Development Platform Attempts to Link Gene Sequence to Expressed Phenotype Under Various Physiological States", Nature Biotech., 16, 393 (1998).
2. Hillenkamp, F., Karas, M., Beavis, R. C., Chait, B. T., "Matrix-Assisted Laser Desorption/Ionization Mass Spectrometry of Biopolymers", Anal. Chem., 63, 1193A (1991).
3. Fenselau, C., "MALDI-MS and Strategies for Protein Analysis", Anal. Chem., 69, 661A (1997).
4. Kebarle, P., Tang, L., "From Ions in Solution to Ions in the Gas Phase", Anal. Chem., 65, 972A (1993).
5. Yates, J. R. III, "Mass Spectrometry and the Age of the Proteome", J. Mass Spectrom., 33, 1 (1998).
6. Klose, J., Kobalz, U., "Two-Dimensional Electrophoresis of Proteins: An Updated Protocol and Implications for a Functional Analysis of the Genome", Electrophoresis, 16, 1034 (1995).
7. Jungblut, P., Thiede, B., Zimny-Amdt, U., Muller, E.-C., Scheler, C., Wittmann-Liebold, B., Otto, A., "Resolution Power of Two-Dimensional Electrophoresis and Identification of Proteins from Gels", Electrophoresis, 17, 839 (1996).
8. Rabilloud, T., "Detecting Proteins Separated by 2-D Gel Electrophoresis", Anal. Chem., 72, 48A (2000).
9. Shevchenko, A., Wilm, M., Vorm, O., Mann, M., "Mass Spectrometric Sequencing of Proteins from Silver-Stained Polyacrylamide Gels", Anal. Chem., 68, 850 (1996).
10. Shevchenko, A., Jensen, O. N., Podtelejnikov, A. V., Sagliocco, F., Wilm, M., Vorm, O., Mortensen, P., Shevchenko, A., Boucherie, H., Mann, M., "Linking Genome and Proteome by Mass Spectrometry: Large-Scale Identification of Yeast Proteins from Two Dimensional Gels", Proc. Natl. Acad. Sci. USA, 93, 14440 (1996).
11. Gygi, S. P., Corthals, G. L., Zhang, Y., Rochon, Y., Aebersold, R., "Evaluation of Two-Dimensional Gel Electrophoresis-Based Proteome Analysis Technology", Proc. Natl. Acad. Sci. USA, 97, 9390 (2000)
12. Smith, R. D., "Probing Proteomes-Secing the Whole Picture", Nature Biotech., 18, 1041 (2000).
13. Burgi, D. S., Chien, R. L., "Optimization in Sample Stacking for High-Performance Capillary Electrophoresis", Anal. Chem., 63, 2042 (1991).
14. Chien, R. L., Burgi, D. S., "On-Colunm Sample Concentration Using Field Amplified in CZE", Anal. Chem., 64, 489A (1992).

15. Burgi, D. S., Chien, R. L., "Sample Stacking of an Extremely Large Injection Volume in High-Performance Capillary Electrophoresis", Anal. Chem., 64, 1046 (1992).
16. Burgi, D. S., Chien, R. L., "On-Line Sample Preconcentration for Capillary Electrophoresis", in "Handbook of Capillary Electrophoresis" (Landers, J. P. ed.), CRC Press, pp. 479 (1997).
17. Xu, J., Gao, J., Locascio, L. E., Lee, C. S., "Integrated Microfluidic System Enabling Rapid Protein Digestion, Peptide Separation, and Protein Identification", Anal. Chem. in press (2001).
18. Henzel, W. J., Billeci, T. M., Stults, J. T., Wong, S. C., "Identifying Proteins from Two-Dimensional Gels by Molecular Mass Searching of Peptide Fragments in Protein Sequence Database", Proc. Natl. Acad. Sci. USA, 90, 5011 (1993).
19. Yates, J. R. III, "Mass Spectrometry and the Age of the Proteome", J. Mass Spectrom., 33, 1 (1998).
20. McCormack, A. L., Schieltz, D. M., Goode, B., Yang, S., Barnes, G., Drubin, D., Yates, J. R. III, "Direct Analysis and Identification of Proteins in Mixtures by LC/MS/MS and Database Searching at the Low-Femtomole Level", Anal. Chem., 69, 767 (1997).
21. Link, A. J., Eng, J., Schieltz, D. M., Carmack, E., Mize, G. J., Morris, D. R., Garvik, B. M., Yates, J. R. III, "Direct Analysis of Protein Complexes Using Mass Spectrometry", Nature Biotech., 17, 676 (1999).
22. Yates, J. R. III, Washburn, M., Wolters, D., "Multi-Dimensional Separations for Protein and Peptide Analysis", presented at the 14$^{th}$ International Symposium on Microscale Separations and Analysis, Boston, Massachusetts, Jan. 13–18, 2001.
23. Gao, J., Xu, J., Locascio, L. E., Lee, C. S., "Integrated Microfluidic System Enabling Rapid Protein Digestion, Peptide Separation, and Protein Identification", Anal. Chem. 73, 2648 (2001).
24. Yang, L., Hofstadler, S. A., Smith, R. D., Lee, C. S., "Characterization of Microdialysis Acidification for Capillary Isoelectric Focusing-Microelectrospray Ionization Mass Spectrometry", Anal. Chem., 70, 4945 (1998).
25. Martynova, L., Locascio, L. E., Gaitan, M., Kramer, G. W., Christensen, R. D., MacCrehan, W. A., "Fabrication of Plastic Microfluid Channels by Imprinting Methods", Anal. Chem., 69, 4783 (1997).
26. Xu, J., Locascio, L. E., Gaitan, M., Lee, C. S., "Room Temperature Imprinting Method for Plastic Microchannel Fabrication", Anal. Chem., 72, 1930 (2000).
27. Tang, Q., Harrata, A. K., Lee, C. S., "Two-Dimensional Analysis of Recombinant E. Coli Proteins Using Capillary Isoelectric Focusing-Electrospray Ionization Mass Spectrometry", Anal. Chem., 69, 3177 (1997).
28. Strahler, J. R., Kuick, R., Hanash, S. M., "Two-Dimensional Polyacrylamdie Gel Electrophoresis of Proteins", in "Protein Structure: A Practical Approach" (Creighton, T. E. ed.), Oxford University Press, pp. 65 (1988).
29. Pasa-Tolic, L., Jensen, P. K., Anderson, G. A., Lipton, M. S., Peden, K. K., Martinovic, S., Tolic, N., Bruce, J. E., Smith, R. D., "High Throughput Proteome-Wide Precision Measurements of Protein Expression Using Mass Spectrometry", J. Am. Chem. Soc., 121, 7949 (1999).
30. Morozov V. N., Morozova T. Y., "Electrospray Deposition as a Method for Mass Fabrication of Mono- and Multicomponent Microarrays of Biological and Biologically Active Substances," Anal. Chem., 71, 3110 (1999).
31. Morozov V. N., Morozova T. Y., "Electrospray Deposition as a Method to Fabricate Functionally Active Protein Films," Anal. Chem., 71, 1415 (1999).
32. Ramsey R. S., Ramsey J. M., "Generating Electrospray from Microchip Devices Using Electroosmotic Pumping" Anal. Chem., 69, 1174 (1997).
33. Oleschuk R. D., Harrison, D. J., "Analytical Microdevices for Mass Spectrometry" Trend in Anal. Chem., 19, 379 (2000).
34. Yan, J. X., Harry, R. A., Spibey, C., Dunn, M. J., "Postelectrophoretic Staining of Proteins Separated by Two-Dimensional Gel Electrophoresis Using SYPRO Dyes", Electrophoresis, 21, 3657 (2000).
35. Gatlin, C. L., Kleemann, G. R., Hays, L. G., Link, A. J., Yates, J. R. III, "Protein Identification at the Low Femtomole Level from Silver-Stained Gels Using a New Fritless Electrospray Interface for Liquid Chromatography Microspray and Nanospray Mass Spectrometry", Anal. Biochem., 263, 93 (1998).
36. Scheler, C., Lamer, S., Pan, Z. M., Li, X. P., Salnikow, J., Jungblut, P., "Peptide Mass Fingerprint Sequence Coverage from Different Stained Proteins on Two-Dimensional Electrophoresis Patterns by Matrix Assisted Laser Desorption/Ionization Mass Spectrometry", Electrophoresis, 19, 918 (1998).
37. Lopez, M. F., Berggren, K., Chernokalakaya, E., Lazarev, A., Robinson, M., Patton, W. F., "A Comparison of Silver Stain and SYPRO Ruby Protein Gel Stain with Respect to Protein Detection in Two-Dimensional Gels and Identification by Peptide Mass Profiling", Electrophoresis, 21, 3673 (2000).
38. Gharahdaghi, F., Weinberg, C. R., Meagher, D. A., Imai, B. S., Mische, S. M., "Mass Spectrometric Identification of Proteins from Silver-Stained Polyacrylamide Gel: A Method for the Removal of Silver Ions to Enhance Sensitivity", Electrophoresis, 20, 601 (1999).
39. Horowitz, P. M., Bowman, S., "Ion-Enhanced Fluorescence Staining of Sodium Dodecyl Sulfate-Polyacrylamide Gels Using Bis(8-p-toluidino-1-naphthalenesulfonate)", Anal. Biochem., 165, 430 (1987).
40. Berggren, K., Chernokalskaya, E., Steinberg, T. H., Kemper, C., Lopez, M. F., Diwu, Z., Haugland, R. P., Patton, W. F., "Background-Free, High Sensitivity Staining of Proteins in One- and Two-Dimensional Sodium Dodecyl Sulfate-Polyacrylamide Gels Using a Luminescent Ruthenium Complex", Electrophoresis, 21, 2509 (2000).
41. Patton, W. F., "A Thousand Points of Light: The Application of Fluorescence Detection Technologies to Two-Dimensional Gel Electrophoresis and Proteomics", Electrophoresis, 21, 1123 (2000).
42. Kelly, J. A., Reddy, K. R., Lee, C. S., "Mechanistic Studies of Post-Capillary Affinity Detection for Capillary Zone Electrophoresis Based on The Biotin-Streptavidin System", Anal. Chem., 69, 5152 (1997).
43. Kelly, J. A. and Lee, C. S., "On-Line Post-Capillary Affinity Detection of Immunoglobulin G Subclasses and Monoclonal Antibody Variants for Capillary Electrophoresis", J. Chromatogr. A, 790, 207 (1997).
44. Ramsamooj, P., Kasid, U., Dritschilo, A, "Differential Expression of Proteins in Radioresistant and Radiosensitive Human Squamous Carcinoma Cells", J. Natl. Cancer Inst., 84, 622 (1992).
45. Wilkins, M. R., Williams, K. L., Appel, R. D., Hochstrasser, D. F., eds., "Proteome Research: New Frontiers in Functional Genomics", pp. 243, Springer, Berlin (1997).
46. Ostergaard, M., Wolf, H., Orntoft, T. E., Celis, J. E., "A Putative Urinary Marker for the Follow-Up of Patients with Bladder Squamous Cell Carcinomas", Electrophoresis, 20, 349 (1999).

47. Page, M. J., Amess, B., Townsend, R. R., Parekh, R., Herath, A., Brusten, L., Zvelebil, M. J., Stein, R. C., Waterfield, M. D., Davies, S. C., O'Hare, M. J., "Proteomic Definition of Normal Human Luminal and Myoepithelial Breast Cells Purified from Reduction Mammoplasties", Proc. Natl. Acad. Sci. USA, 96, 12589 (1999).
48. Wilm, M., Vorm, O., Mann, M., "Femtomole Sequencing of Proteins from Polyacrylamide Gels by Nano-Electrospray Mass Spectrometry", Nature, 379, 466 (1996).
49. Lottspeich, F., "Proteome Analysis: A Pathway to the Functional Analysis of Proteins", Angew. Chem. Int. Ed., 38, 2476 (1999).
50. Pandey, A., Mann, M., "Proteomics to Study Genes and Genomes", Nature, 405, 837 (2000).
51. Ogorzalek Loo, R. R., Stevenson, T. I., Mitchell, C., Loo, J. A., Andrews, P. C., "Mass Spectrometry of Proteins Directly from Polyacrylamide Gels", Anal. Chem., 68, 1910 (1996).
52. Vestling, M. M., Fenselau, C., "Poly(vinylidene difluoride) Membranes as the Interface between Laser Desorption Mass Spectrometry, Gel Electrophoresis, and In Situ Proteolysis", Anal. Chem., 66, 471 (1994).
53. Strupat, K., Karas, M., Hillenkamp, F., Eckerskorn, C., Lottspelch, F., "Matrix-Assisted Laser Desorption Ionization Mass Spectrometry of Proteins Electroblotted after Polyacrylamide Gel Electrophoresis", Anal. Chem., 66, 464 (1994).
54. Liang, X., Bai, J., Liu, Y. H., Lubman, D. M., "Characterization of SDS-PAGE-Separated Proteins by Matrix-Assisted Laser Desorption/Ionization Mass Spectrometry", Anal. Chem., 68, 1012 (1996).
55. Eckerskorn, C., Strupat, K., Schleuder, D., Hochstrasser, D., Sanchez, J. C., Lottspeich, F., Hillenkamp, F., "Analysis of Proteins by Direct-Scanning Infrared-MALDI Mass Spectrometry After 2-D PAGE Separation and Electroblotting", Anal. Chem., 69, 2888 (1997),
56. Ekstrom, S., Onnerfjord, P., Nilsson, J., Bengtsson, M., Laurell, T., Marko-Varga, G., "Integrated Microanalytical Technology Enabling Rapid and Automated Protein Identification", Anal. Chem., 72, 286 (2000).
57. Wang, C., Oleschuk, R., Ouchen, F., Li, J., Thibault, P., Harrison, D. J., "Integration of Immobilized Trypsin Bead Beds for Protein Digestion within a Microfluidic Chip Incorporating Capillary Electrophoresis Separations and an Electrospray Ionization Mass Spectrometry Interface", Rapid Commun. Mass Spectrom., 14, 1377 (2000).
58. Binz, P.-A., Muller, M., Walther, D., Bienvenut, W. V., Grass, R., Hoogland, C., Bouchet, G., Gasteiger, E., Fabbretti, R., Gay, S., Palagi, P., Wilkins, M. R., Rouge, V., Tonella, L., Paesano, S., Rossellat, G., Karmime, A., Bairoch, A., Sanchez, J.-C., Appel, R. D., Hochstrasser, D. F., "A Molecular Scanner to Automate Proteomic Research and to Display Proteome Images", Anal. Chem., 71, 4981 (1999).
59. Bienvenut, W. V., Sanchez, J. C., Karmime, A., Rouge, V., Rose, K., Binz, P. A., Hochstrasser, D. F., "Toward a Clinical Molecular Scanner for Proteome Research: Parallel Protein Chemical Processing Before and During Western Blot", Anal. Chem., 71, 4800 (1999).
60. Steinberg, T. H., Haugland, R. P., Singer, V. L., "Applications of SYPRO Orange and SYPRO Red Protein Gel Stains", Anal. Biochem., 239, 238 (1996).
61. Hjerten, S., Zhu, M. D., "Adaptation of the Equipment for High-Performance Electrophoresis to Isoelectric Focusing", J. Chromatogr., 346, 265 (1985).
62. Hjerten, S., Elenbring, K., Kilar, F., Liao, J. L., Chen, A. J. C., Siebert, C. J., Zhu, M. D., "Carrier-Free Zone Electrophoresis, Displacement Electrophoresis, and Isoelectric Focusing in a High-Performnance Electrophoresis Apparatus", J. Chromatogr., 403, 47 (1987).
63. Kilar, F., Hjerten, S., "Fast and High Resolution Analysis of Human Serum Transferrin by High Performance Isoelectric Focusing in Capillaries", Electrophoresis, 10, 23 (1989).
64. Huang, X., Gordon, M. J., Zare, R. N., "Current-Monitoring Method for Measuring the Electroosmotic Flow-Rate in Capillary Zone Electrophoresis", Anal. Chem., 60, 1837 (1988).
65. Yefimov, S., Yergey, A. L., Chrambach, A., "Transfer of SDS-Proteins from Gel Electrophoretic Zones into Mass Spectrometry, Using Electroelution of the Band into Buffer Without Sectioning of the Gel", J. Biochem. Biophys. Methods, 42, 65 (2000).
66. Yefimov, S., Sjomeling, C., Yergey, A. L., Li, T., Chrambach, A., "Recovery of Sodium Dodecyl Sulfate-Proteins from Gel Electrophoretic Bands in a Single Electroelution Step for Mass Spectrometry Analysis", Anal. Biochem., 284, 288 (2000).
67. Galvani, M., Hamdan, M., "Electroelution and Passive Elution of a-globulins from Sodium Dodecyl Sulfate Polyacrylamide Gel Electrophoresis Gels for Matrix-Assisted Laser Desorption/Ionization Time-of-Flight Mass Spectrometry", Rapid Commun. Mass Spectrom., 14, 721 (2000).
68. Clarke, N. J., Li, F., Tomlinson, A. J., "One Step Microelectroelution Concentration Method for Efficient Coupling of Sodium Dodecylsulfate Gel Electrophoresis and Matrix-Assisted Laser Desorption Time-of-Flight Mass Spectrometry for Protein Analysis", J. Am. Soc. Mass Spectrom., 9, 88 (1998).
69. Tomlinson, A. J., Benson, L. M., Braddock, W. D., Oda, R. P., Naylor, S., "Improved On-Line Membrane Preconcentration-Capillary Electrophoresis", J. High Resol. Chromatogr., 18, 381 (1995).
70. Timperman, A. T., Aebersold, R., "Peptide Electroextraction for Direct Coupling of In-Gel Digests with Capillary LC-MS/MS for Protein Identification and Sequencing", Anal. Chem., 72, 4115 (2000).
71. Locke, S., Figeys, D., "Techniques for the Optimization of Proteome Strategies Based on Head Column Stacking Capillary Electrophoresis", Anal. Chem., 72, 2684 (2000).
72. Kebarle, P., Ho, Y., "The Electrolytic Nature of Electrospray", in "Electrospray Ionization Mass Spectrometry: Fundamentals, Instrumentation, and Applications"(Cole, R. B. ed.), John Wiley & Sons, pp. 3 (1997).
73. Yang, L., Hofstadler, S. A., Smith, R. D., Lee, C. S., "Characterization of Microdialysis Acidification for Capillary Isoelectric Focusing-Microelectrospray Ionization Mass Spectrometry", Anal. Chem., 70, 4945 (1998).
74. Guttman, A., Ronai, Z., Csapo, Z., Gerstner, A., Sasvari-Szekely, M., "Rapid Analysis of Covalently and Non-Covalently Fluorophore-Labeled Proteins Using Ultra-Thin-Layer Sodium Dodecylsulfate Gel Electrophoresis", J. Chromatogr. A, 894, 329 (2000).
75. Csapo, Z., Gerstner, A., Savari-Szekely, M., Guttman, A., "Automated Ultra-ThinLayer SDS Gel Electrophoresis of Proteins Using Noncovalent Fluorescent Labeling", Anal. Chem., 72, 2519 (2000).
76. Strahler, J. R., Kuick, R., Hanash, S. M., "Two-Dimensional Polyacrylamdie Gel Electrophoresis of Proteins", in "Protein Structure: A Practical Approach" (Creighton, T. E. ed.), Oxford University Press, pp. 65 (1988).
77. Togawa et al., U.S. Pat. No. 5,587,062
78. Gombocz et al., U.S. Pat. No. 5,217,591
79. Gombocz et al., U.S. Pat. No. 5,275,710
80. Doering et al., U.S. Pat. No. 5,102,518
81. Peck et al., U.S. Pat. No. 4,576,702
82. Liao et al., U.S. Pat. No. 5,505,831
83. Kambara et al., U.S. Pat. 5,541,420 (1996)
84. Yefimov et al., 2000, "Transfer of SDS-proteins from gel electrophoretic zones into mass spectrometry, using electroelution of the band into buffer without sectioning of the gel" *J Biochem. Biophys. Methods* 42: 65–78

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims.

We claim:

1. A microfluidic apparatus for performing gel protein extractions, comprising:
   a) an apparatus housing overlaid with an apparatus cover, wherein the housing has disposed therein a gel containing one or more proteins to be extracted and an electrolyte solution;
   b) one or more fluidic channels containing an electrolyte solution, wherein the one or more fluidic channels have a first end and a second end, and wherein the first end is disposed through the apparatus cover and is secured in position at or near a gel interface;
   c) one or more outlet reservoirs having disposed therein an electrolyte solution, a first end of at least one outlet electrode, and the second end of the one or more fluidic channels; and
   d) a high voltage power supply attached to a second end of the at least one outlet electrode for applying an electric field across the length of the one or more fluidic channels.

2. The apparatus of claim 1, wherein a ground electrode is connected to the apparatus housing.

3. The apparatus of claim 1, wherein each of the one or more fluidic channels is connected to the high voltage power supply through an array of switches allowing one or more individual fluidic channels to be selected for extraction independently from other of the one or more fluidic channels.

4. The apparatus of claim 1, wherein each of the one or more fluidic channels comprises:
   a) one or more fluidic extraction channels containing an electrolyte solution, wherein the one or more fluidic extraction channels have a first end and a second end, and wherein the first end is disposed through the apparatus cover and is secured in position at the gel interface; and
   b) one or more fluidic holding channels containing an electrolyte solution, wherein the one or more fluidic holding channels have a first end and a second end, and wherein the first end terminates in the one or more fluidic extraction channels, and wherein the second end of the one or more fluidic holding channels is disposed in the one or more outlet reservoirs.

5. The apparatus of claim 1 wherein a detector is near the one or more outlet reservoirs for monitoring extracted proteins.

6. The apparatus of claim 1, wherein the one or more fluidic channels are capillaries.

7. The apparatus of claim 6, wherein the capillaries are fused silica capillaries.

8. The apparatus of claim 6, wherein the capillaries have an outer diameter of between about 100 µm and about 500 µm and an inner diameter of between about 5 µm and about 100 µm.

9. The apparatus of claim 6, wherein the capillaries are between about 1 cm and about 50 cm long.

10. The apparatus of claim 1, wherein the one or more fluidic channels are microscale channels.

11. The apparatus of claim 1, wherein the one or more fluidic channels are microfluidic channels formed in a planar glass substrate.

12. The apparatus of claim 1, wherein the one or more fluidic channels are microfluidic channels formed in a planar plastic substrates.

13. The-apparatus of claim 1, wherein the one or more fluidic channels are of a diameter which allows them to extract the one or more proteins in the gel in about two minutes or less.

14. The apparatus of claim 1, wherein the one or more fluidic channels are of a diameter which allows them to extract the one or more proteins in the gel in about ten minutes or less.

15. The apparatus of claim 1, wherein the at least one outlet electrode is constructed of platinum.

16. The apparatus of claim 1, wherein the at least one outlet electrode is constructed of gold.

17. The apparatus of claim 1, wherein the at least one outlet electrode is a thin film metal integrated into a glass substrate.

18. The apparatus of claim 1, wherein the at least one outlet electrode is a thin film metal integrated into a plastic substrate.

19. The apparatus of claim 1, wherein the electric field across the one or more fluidic channels is between about 100 V/cm and about 1000 V/cm.

20. The apparatus of claim 1, wherein the apparatus cover and the apparatus housing create a gel chamber compartment that is pressurizable.

21. A method of transferring one or more proteins from a gel, comprising:
   a) contacting a first end of one or more fluidic channels containing an electrolyte solution to one or more locations in a gel containing one or more proteins, wherein:
      1) the gel is disposed within an apparatus housing overlaid with an apparatus cover and the housing has disposed therein an electrolyte solution and has attached thereto a ground electrode;
      2) the one or more fluidic channels have a first end and a second end;
      3) the first end of the one or more fluidic channels is disposed through the apparatus cover and is secured in position at or near a gel interface;
   b) disposing the second end of the one or more fluidic channels in one or more outlet reservoirs, wherein:
      1) the one or more outlet reservoirs have disposed therein an electrolyte solution and a first end of an outlet electrode; and 2) a high voltage power supply is attached to the outlet electrode;

c) applying a high electric field along the length of the one or more fluidic channels, thereby extracting the one or more proteins from the gel and into the first end of the one or more fluidic channels;

d) concentrating the one or more proteins near the first end of the one or more fluidic channels by electrophoretic stacking, and e) transferring the one or more proteins from the first end of the one or more fluidic channels toward the second end of the one or more fluidic channels.

22. The method of claim 21, wherein the one or more proteins are transferred from the first end of the one or more fluidic channels toward the second end of the one or more fluidic channels in step (e) by a method further comprising:

a) stopping the high electric field across the one or more fluidic channels;

b) removing the first end of the one or more fluidic channels from the gel interface and transferring the first end of the one or more fluidic channels into a reservoir of fresh electrolyte solution; and c) reapplying the high electric field to the one or more fluidic channels so that the one or more proteins are transferred from the first end of the one or more fluidic channels toward the second end of the one or more fluidic channels for at least one of analysis or collection.

23. The method of claim 21, wherein the one or more proteins are transferred from the first end of the one or more fluidic channels toward the second end of the one or more fluidic channels in step (e) by a method further comprising:

a) stopping the high electric field across the one or more fluidic channels;

b) raising the one or more fluidic channels slightly above the gel interface; and c) pressurizing a compartment created by the apparatus housing and the apparatus cover so that the one or more proteins are transferred from the first end of the one or more fluidic channels toward the second end of the one or more fluidic channels for at least one of collection or analysis.

24. The method of claim 21, wherein the one or more proteins are transferred from the first end of the one or more fluidic channels toward the second end of the one or more fluidic channels in step (e) by a method further comprising allowing the high electric field to continually transfer the one or more proteins from the first end of the one or more fluidic channels to the second end of the one or more fluidic channels while the first end of the one or more fluidic channels is still contacted to the gel.

25. The method of claim 21, wherein the one or more proteins are transferred from the first end of the one or more fluidic channels toward the second end of the one or more fluidic channels in step (e) by a method further comprising:

a) stopping the high electric field across the one or more fluidic channels;

b) raising the one or more fluidic channels slightly above the gel interface; and c) applying a negative pressure at the second end of the one or more fluidic channels relative to a compartment pressure within the apparatus housing so that the one or more proteins are transferred from the first end of the one or more fluidic channels toward the second end of the one or more fluidic channels for at least one of collection or analysis.

26. The method of claim 21, wherein one or more instruments are located on or near the one or more fluidic channels to analyze the one or more proteins.

27. The method of claim 26, wherein the one or more instruments are a UV detector or a fluorescence detector.

28. The method of claim 21, wherein the one or more proteins are subject to digestion.

29. The method of claim 28, wherein the one or more proteins are subject to digestion before transfer to the one or more fluidic channels.

30. The method of claim 29, wherein digestion includes in-gel digestion prior to transfer.

31. The method of claim 30, wherein the digestion is performed with a prototypic enzyme.

32. The method of claim 31, wherein the prototypic enzyme is trypsin.

33. The method of claim 29, wherein the one or more digested proteins are fluidically transferred into a mass spectrometer from the first end of the one or more fluidic channels.

34. The method of claim 29, wherein the one or more digested proteins are fluidically transferred into a mass spectrometer from the second end of the one or more fluidic channels.

35. The method of claim 29, wherein the one or more digested proteins are fluidically transferred from the first end of the one or more fluidic channels onto a MALDI target plate for further analysis by a mass spectrometer.

36. The method of claim 29, wherein the one or more proteins are fluidically transferred from the second end of the one or more fluidic channels onto a MALDI target plate for further analysis by a mass spectrometer.

37. The method of claim 28, wherein the one or more proteins are subject to digestion during transfer to the one or more fluidic channels.

38. The method of claim 37, wherein the one or more proteins undergo digestion in a membrane containing immobilized prototypic enzymes positioned between the gel and the first end of the one or more fluidic channels.

39. The method of claim 38, wherein the prototypic enzymes include trypsin.

40. The method of claim 37, wherein the one or more digested proteins are fluidically transferred into a mass spectrometer from the first end of the one or more fluidic channels.

41. The method of claim 37, wherein the one or more digested proteins are fluidically transferred into a mass spectrometer from the second end of the one or more fluidic channels.

42. The method of claim 37, wherein the one or more digested proteins are fluidically transferred from the first end of the one or more fluidic channels onto a MALDI target plate for further analysis by a mass spectrometer.

43. The method of claim 37, wherein the one or more digested proteins are fluidically transferred from the second end of the one or more fluidic channels onto a MALDI target plate for further analysis by a mass spectrometer.

44. The method of claim 28, wherein the one or more proteins are subject to digestion after transfer to the one or more fluidic channels.

45. The method of claim 44, wherein the one or more proteins are transferred directly from the one or more fluidic channels to a micro membrane reactor containing prototypic enzymes for digestion.

46. The method of claim 45, wherein the prototypic enzymes include trypsin.

47. The method of claim 44, wherein the one or more proteins is are transferred directly from the one or more fluidic channels to a column reactor containing particles or beads immobilized with prototypic enzymes for digestion.

48. The method of claim 47, wherein the prototypic enzymes include trypsin.

49. The method of claim 44, wherein the one or more fluidic channels contain particles or beads immobilized with prototypic enzymes for digestion.

50. The method of claim 49, wherein the prototypic enzymes include trypsin.

51. The method of claim 44, wherein prototypic enzymes for protein digestion are contained in solution within the one or more fluidic channels.

52. The method of claim 51, wherein the prototypic enzymes include trypsin.

53. The method of claim 44, wherein the one or more digested proteins are fluidically transferred into a mass spectromete from the first end of the one or more fluidic channels.

54. The method of claim 44, wherein the one or more digested proteins are fluidically transferred into a mass spectrometer from the second end of the one or more fluidic channels.

55. The method of claim 44, wherein the one or more digested proteins are fluidically transferred from the first end of the one or more fluidic channels onto a MALDI target plate for further analysis by a mass spectrometer.

56. The method of claim 44, wherein the one or more digested proteins are fluidically transferred from the second end of the one or more fluidic channels onto a MALDI target plate for further analysis by a mass spectrometer.

57. The method of claim 21, wherein the one or more proteins are denatured in sodium dodecyl sulfate.

58. The method of claim 21, wherein the one or more fluidic channels are capillaries.

59. The method of claim 21, wherein the one or more fluidic channels are microfluidic channels formed in a planar glass substrate.

60. The method of claim 21, wherein the one or more fluidic channels are microfluidic channels formed in a planar plastic substrate.

61. The method of claim 21, wherein the one or more fluidic channels are coated with hydrophilic polymers.

62. The method of claim 61, wherein the hydrophilic polymers include polyacrylamide.

63. The method of claim 21, wherein the one or more fluidic channels are arranged in an array, and the array contacts the gel.

64. The method of claim 21, wherein the high electric field within each of the one or more fluidic channels is individually addressable for extraction independently from other of the one or more fluidic channels.

65. The method of claim 21, wherein the one or more fluidic channels may be positioned sequentially or simultaneously at various gel locations using a manual or automated positioning system, enabling individual or groups of the one or more fluidic channels within the array to sequentially or simultaneously extract multiple proteins from the various gel locations using a single extraction apparatus.

66. The method of claim 21, wherein the electrolyte solution contains Tris-HC 1 at a concentration of at most about 25 mM Tris-HCL at about pH 6.8.

67. The method of claim 21, wherein the gel is made of polyacrylamide or agarose.

68. The method of claim 21, wherein the gel is between about 1 mm and about 100 μm thick.

69. The method of claim 21, wherein the gel is a gradient gel in the range of about 4% to about 20% polyacrylamide.

70. The method of claim 21, wherein the gel is a Tris/Tricine SDS polyacrylamide gel.

71. The method of claim 21, wherein the gel was used to perform 1D or 2D gel electrophoresis.

72. The method of claim 21, wherein locations to place the first end of the one or more fluidic channels are visualized or imaged.

73. The method of claim 72, wherein the visualization is performed with SYPRO fluorescent dyes.

74. The method of claim 72, wherein the visualization is perfomied with Coomassie blue.

75. The method of claim 72, wherein the visualization is performed with silver staining.

* * * * *